US010927773B2

(12) United States Patent
Gieger

(10) Patent No.: US 10,927,773 B2
(45) Date of Patent: Feb. 23, 2021

(54) DEVICE FOR OPERATING AN ENGINE

(71) Applicant: CleanTech Swiss AG, Wangen (CH)

(72) Inventor: Werner Gieger, Nuolen (CH)

(73) Assignee: CleanTech Swiss AG, Wangen (CH)

( * ) Notice: Subject to any disclaimer, the term of this patent is extended or adjusted under 35 U.S.C. 154(b) by 0 days.

(21) Appl. No.: 16/302,164

(22) PCT Filed: May 23, 2017

(86) PCT No.: PCT/EP2017/062372
§ 371 (c)(1),
(2) Date: Nov. 16, 2018

(87) PCT Pub. No.: WO2017/202826
PCT Pub. Date: Nov. 30, 2017

(65) Prior Publication Data
US 2019/0145327 A1    May 16, 2019

(30) Foreign Application Priority Data

May 24, 2016    (EP) ..................................... 1617068

(51) Int. Cl.
*F02D 41/00* (2006.01)
*F02D 19/02* (2006.01)
(Continued)

(52) U.S. Cl.
CPC ......... *F02D 19/024* (2013.01); *F02D 19/023* (2013.01); *F02D 19/026* (2013.01);
(Continued)

(58) Field of Classification Search
CPC ............. F02D 19/0642; F02D 19/0644; F02D 19/0647; F02D 19/066
See application file for complete search history.

(56) References Cited

U.S. PATENT DOCUMENTS 5,131,228 A * 7/1992 Mochizuki ............. F02M 37/18
60/602
5,179,926 A * 1/1993 Ament ................... G01N 27/06
123/494

(Continued)

FOREIGN PATENT DOCUMENTS

CN    101370681 A    2/2009
DE    25 44 444 A1    4/1977
(Continued)

OTHER PUBLICATIONS

English Translation of the International Preliminary Report on Patentability dated Nov. 27, 2018.
(Continued)

*Primary Examiner* — Kevin R Steckbauer
(74) *Attorney, Agent, or Firm* — Renner, Otto, Boisselle & Sklar, LLP

(57) ABSTRACT

The invention relates to a device and a method for ascertaining an injection time and/or an amount of a liquefied gas fuel—such as liquefied petroleum gas (LPG), natural gas (CNG), liquefied natural gas (LNG), biogas or hydrogen ($H_2$)—to be delivered to a cylinder of an engine (19) in order to operate the engine (19) in a bivalent or trivalent fuel operating mode, said device being designed in such a way that the ascertained injection time of the liquefied gas fuel is dependent on an ascertained calorific power or an ascertained gas mixture characteristic. A gas mixture analysis module (7) is used for optimizing combustion. A gas start mechanism allows a vehicle to be started on gas power even at low temperatures.

16 Claims, 9 Drawing Sheets

(51) Int. Cl.
*F02D 41/06* (2006.01)
*F02D 41/30* (2006.01)
*F02M 21/02* (2006.01)
*F02D 19/08* (2006.01)
*G01N 33/22* (2006.01)

(52) U.S. Cl.
CPC ....... *F02D 19/087* (2013.01); *F02D 41/0025* (2013.01); *F02D 41/0027* (2013.01); *F02D 41/062* (2013.01); *F02D 41/30* (2013.01); *F02M 21/0215* (2013.01); *F02D 2200/0611* (2013.01); *F02D 2400/11* (2013.01); *G01N 33/225* (2013.01); *Y02T 10/30* (2013.01)

(56) References Cited

U.S. PATENT DOCUMENTS

| | | | | |
|---|---|---|---|---|
| 5,357,927 | A * | 10/1994 | Saito | F02D 19/0686 123/406.54 |
| 5,377,645 | A * | 1/1995 | Moore | F02M 21/0287 123/525 |
| 5,379,740 | A * | 1/1995 | Moore | F02D 19/0628 123/478 |
| 5,390,640 | A * | 2/1995 | Saito | F02N 19/001 123/491 |
| 5,402,763 | A * | 4/1995 | Saito | F02D 19/084 123/491 |
| 6,612,269 | B2 * | 9/2003 | Heffel | F02D 19/087 123/1 A |
| 6,769,418 | B1 | 8/2004 | Reddy | |
| 7,874,275 | B1 * | 1/2011 | Herzer | F02M 21/06 123/195 A |
| RE42,876 | E * | 11/2011 | Heffel | F02B 43/00 123/1 A |
| 8,073,636 | B2 * | 12/2011 | Bauer | F02D 19/027 702/24 |
| 8,516,991 | B2 * | 8/2013 | Tanno | F02D 19/061 123/305 |
| 8,640,681 | B2 * | 2/2014 | Kawai | F02D 41/0002 123/575 |
| 9,261,466 | B2 * | 2/2016 | Soergel | F02M 25/0228 |
| 9,689,323 | B2 * | 6/2017 | Ferrie | G01N 33/2847 |
| 10,260,432 | B1 * | 4/2019 | Kim | F02D 41/1401 |
| 2002/0029770 | A1 * | 3/2002 | Heffel | F02D 19/029 123/527 |
| 2008/0060627 | A1 * | 3/2008 | Bromberg | F02B 51/00 123/575 |
| 2008/0255753 | A1 * | 10/2008 | Spivak | F02D 19/061 701/103 |
| 2009/0097525 | A1 * | 4/2009 | Ibuki | F02D 35/025 374/29 |
| 2009/0314267 | A1 * | 12/2009 | Kawai | F02D 41/2454 123/674 |
| 2010/0268443 | A1 * | 10/2010 | Gurin | F02M 23/12 701/103 |
| 2011/0030664 | A1 * | 2/2011 | Schneider | F02D 41/1456 123/703 |
| 2011/0083645 | A1 * | 4/2011 | Herzer | F02M 21/06 123/557 |
| 2011/0083759 | A1 * | 4/2011 | Herzer | F02M 21/0221 137/561 R |
| 2011/0088657 | A1 * | 4/2011 | Tanno | F02D 19/0649 123/305 |
| 2011/0218726 | A1 | 9/2011 | Bowling et al. | |
| 2013/0317724 | A1 * | 11/2013 | Ferrie | G01N 33/2847 701/104 |
| 2019/0093572 | A1 * | 3/2019 | Kim | F02D 19/10 |
| 2019/0323443 | A1 * | 10/2019 | Lothgren | F02D 19/029 |

FOREIGN PATENT DOCUMENTS

| | | | |
|---|---|---|---|
| DE | 196 22 105 A1 | 12/1996 | |
| DE | 10 2004 016159 A1 | 11/2005 | |
| DE | 10 2006 022 357 B3 | 10/2007 | |
| DE | 10 2006 022357 B3 | 10/2007 | |
| DE | 10 2006 030 495 A1 | 1/2008 | |
| DE | 10 2010 039 844 A1 | 3/2012 | |
| DE | 10 2011 075 223 A1 | 11/2012 | |
| DE | 10 2012 100 115 B4 | 7/2013 | |
| DE | 10 2012 017 440 A1 | 3/2014 | |
| DE | 10 2012 017440 A1 | 3/2014 | |
| EP | 0 894 959 A2 | 2/1999 | |
| EP | 0894959 A2 * | 2/1999 | ......... F02M 21/0221 |
| EP | 2 966 284 A1 | 1/2016 | |
| WO | 2007/019649 A1 | 2/2007 | |
| WO | 2007/092142 A2 | 8/2007 | |
| WO | WO 2009/141512 A1 | 11/2009 | |
| WO | WO-2009141512 A1 * | 11/2009 | ............ F02M 21/06 |
| WO | WO 2011/136694 A1 | 3/2011 | |
| WO | 2011/101394 A1 | 8/2011 | |
| WO | 2014/166534 A1 | 10/2014 | |

OTHER PUBLICATIONS

International Search Report and Written Opinion for corresponding Patent Application No. PCT/EP2017/062372 dated Oct. 18, 2017.
Dr. Merten Joost, et al. "Gassensoren Informatik Seminar Sommersemester 2010," URL: https://www.uni-koblenz.de/physik/informatik/Sensoren/gas.pdf, Jun. 1, 2010, p. 4 to p. 8.

* cited by examiner

Example:

Input parameters:
A=9; B=2

Output parameter:
→ C=12

DEVICE FOR OPERATING AN ENGINE

The invention concerns an apparatus and method for operating an engine in a bivalent or trivalent fuel mode with liquefied gas fuel such as autogas (LPG), natural gas (CNG), liquefied natural gas (LNG), biogas or hydrogen ($H_2$).

In a gasoline or diesel engine, an engine control unit usually ensures that gasoline or diesel is supplied to the engine for a proper combustion process.

If a vehicle is to be retrofitted for operation with LPG or CNG, an add-on control unit is usually installed in the vehicle so that the engine can also be operated with LPG or CNG.

The documents DE102010039844A1, DE102011075223A1, DE10201210011564, WO2014166534A1, WO2011101394A1, DE201010008289A1, DE102012017440A1, DE102006030495A1, WO2007092142A2 and DE102006022357B3 discloses retrofittable devices for operating an engine with LPG, CNG, $H_2$ and the like.

However, there is a need to improve the combustion process when operating an engine with LPG, CNG, $H_2$ or the like in terms of the quality of the combustion process, pollutant emissions and/or starting a gasoline or diesel engine when operating with LPG, CNG, $H_2$ or the like, particularly at cold outside temperatures.

It is therefore object of the invention to provide a further developed apparatus, add-on control unit, a gas-start-system and a method.

The problem is solved by an apparatus according to the main claim and a method, a Gas-mixture-analysis-module and a gas-start-system of the independent claims. The features described in the introduction can, alone or in combination, be combined with one of the following matters of the invention.

The problem is solved by an apparatus for determining a blow-in time and/or an amount of liquefied gas fuel such as autogas (LPG), natural gas (CNG), liquefied natural gas (LNG), biogas or hydrogen ($H_2$) to be supplied to a cylinder of an engine for operating the engine in a bivalent or trivalent fuel mode, wherein the apparatus is arranged such that the determined blow-in time of the liquefied gas fuel is dependent on a determined calorific value or a determined gas-mixture-characteristic value.

Particularly, the apparatus is suitable for determining a blow-in time, particularly for a first liquefied gas fuel and/or an amount of a particularly second liquefied gas fuel to be supplied to a cylinder of an engine for operating the engine in a bivalent or trivalent fuel mode, the apparatus being arranged such that the determined blow-in time of the liquefied gas fuel depends on a determined calorific value or a determined gas-mixture-characteristic value, the particularly first and second liquefied gas fuel being for example autogas (LPG), natural gas (CNG), liquefied natural gas (LNG), biogas or hydrogen ($H_2$).

Blow-in time means blow-in time of (time duration of blowing) an especially first liquefied gas fuel, preferably LPG, CNG, LNG or biogas, into the cylinder of the engine per work cycle.

Amount to be supplied means volume of a especially second liquefied gas fuel, preferably hydrogen, which is supplied to the cylinder. Basically, the amount to be supplied can also be described by the blow-in time at a constant supply speed or flow rate of the liquefied gas fuel to the cylinder.

The apparatus can thus be operated with only one liquefied gas fuel, like e.g. LPG, or exactly two liquefied gas fuels, like e.g. LPG and hydrogen.

Liquid fuel is a fuel present in the liquid phase at room temperature and normal ambient pressure of one bar.

Liquid fuel includes especially gasoline, petrol, diesel, biodiesel and vegetable oils used as fuel.

Liquefied gas fuel is a fuel that is present particularly exclusively in the gaseous phase at room temperature and normal ambient pressure of one bar and can preferably only be converted into liquid phase under high pressure, i.e. pressure particularly greater than two bars.

Liquefied gas fuel covers autogas (LPG, Liquefied Petroleum Gas), petroleum gas or natural gas (CNG), liquefied natural gas (LNG; Liquefied Natural Gas), biogas and hydrogen ($H_2$).

Monovalent fuel mode means operating an engine to drive a vehicle with only one fuel.

Bivalent fuel mode means operating an engine to drive a vehicle with exactly two different fuels simultaneously, i.e. two different fuels are burned simultaneously in the engine or in a cylinder. Thus, for example, bivalent fuel mode is when operating with exactly one liquefied gas fuel and exactly one liquid fuel, or alternatively with exactly two different liquefied gas fuels. Bivalent fuel mode is, for example, when operating with diesel and LPG, or LPG and hydrogen.

Trivalent fuel mode means operating an engine to drive a vehicle with exactly three different fuels simultaneously, i.e. three different fuels are burned simultaneously in the engine or in a cylinder. Thus, for example, trivalent fuel mode is when operating with exactly two different liquefied gas fuels and exactly one liquid fuel. Trivalent fuel mode is, for example, operating with diesel, LPG and hydrogen.

The determined blow-in time being dependent on a determined calorific value or a determined gas-mixture-characteristic value means that the calorific value or determined gas-mixture-characteristic value are taken into account when determining the blow-in time, in particular as a variable input parameter in a defined determination method.

Determined calorific value or determined gas-mixture-characteristic value means that the calorific value or gas-mixture-characteristic value were determined either by the apparatus or the add-on control unit themselves. Alternatively, the calorific value or gas-mixture-characteristic have also been determined by a module connected via an interface and transmitted to the apparatus or the add-on control unit.

Preferably, a module, i.e. the $H_2$-module, the safety-module, the lambda-offset-module and/or the gas-mixture-analysis-module, is designed as an independent electronic component with at least two analog or digital data interfaces and one analog or digital circuit.

Alternatively, one or more of the modules, i.e. $H_2$-module, safety-module, lambda-offset-module and/or gas-mixture-analysis-module, can be integrated in the apparatus or the add-on control unit, i.e. for example as an integrated digital signal processor or as an analog circuit within the housing of the add-on control unit or integrated in form of a program code on a storage medium of the add-on control unit, which causes a processor of the add-on control unit to perform steps defined by the program code.

Typical components of a module, i.e. the $H_2$-module, safety-module, lambda-offset-module and/or gas-mixture-analysis-module, are for an analog embodiment an amplifier, filter, rectifier, analog-to-digital-converter, digital-to-analog-converter, data or signal line interface and/or mixer, and for a digital embodiment logic gates, microprocessors, analogto-digital-converter, digital-to-analog-converter, data or signal line interface and/or data memory.

The calorific value is a measure of the specific thermal energy per measurement unit contained in a substance or, here, the gas mixture 2, 21.

Particularly, the calorific value corresponds to the calorific value $H_S$.

The calorific value $H_S$ can be expressed in kWh/m³, kWh/kg or kWh/l. Preferably, the calorific value $H_S$ is related or indicated to the volume in a specified or normalized state, thus especially at a certain temperature and certain pressure. Particularly, these conditions may include normal ambient pressure of 1 bar, room temperature of e.g. 25° C., for CNG and biogas relative humidity of 100% of all gases involved before and after combustion and/or the liquid water formed after combustion with room temperature of e.g. 25° C. For example, the calorific value $H_S$ can be calculated or indicated such that the calorific value $H_S$ of propane is exactly or approximately 28.095 kWh/m³, 14.06 KWh/kg or 7.17 kWh/l. Alternatively or additionally, reference is made to DIN 51857, DIN EN ISO 6976 and/or DIN 18599 with regard to the calorific value $H_S$.

The gas-mixture-characteristic value is a numerical value, which was assigned from a large number of numerical values, particularly stored in a memory, based on at least one measured parameter and/or at most five measured parameters of the current gas mixture and has thus been determined. Preferred are exactly three measured parameter of the current gas mixture.

Measured parameter of the current gas mixture means a measured value, measured by a sensor, whose amount correlates with a property of the gas mixture. A measured parameter can be the result of data processing of a measured value.

Particularly, the gas-mixture-characteristic value can be converted, preferably by a defined algorithm with one or more conversion constants and/or one or more conversion factors, into the calorific value, a variable approximating the calorific value, or a variable corresponding approximately to the calorific value.

Particularly, the gas-mixture-characteristic value is suitable for shifting the blow-in time or a gas-blow-in-look-up-table or a gas-blow-in-curve of a gas-blow-in-look-up-table towards rich or lean, i.e. in direction of longer blow-in time or shorter blow-in time. The gas-blow-in-look-up-table will be described later in more detail.

Rich and lean is related to the combustion of fuel in the cylinder of the engine and can be explained using the lambda value, also named λ or lambda, as follows. Lambda describes the combustion-air ratio—also called air ratio or air number—and is a dimensionless index from the combustion theory, which indicates the mass ratio of air and fuel in a combustion process. From this number, conclusions can be drawn about the combustion process, temperatures, pollutant formation and efficiency.

If lambda=1, then there is a complete combustion, i.e. all fuel molecules react completely with the atmospheric oxygen, without missing oxygen or remaining unburned fuel, thus having a complete combustion.

Lambda<1 (e.g. 0.9) means lack of air, i.e. "rich" or rich mixture.

Lambda>1 (e.g. 1.1) means excess air, i.e. "lean" or poor mixture.

For example, lambda=1.1 means that 10% more air participates in combustion than would be necessary for the stoichiometric reaction.

Because the calorific value depends on the composition of the gas components of the particularly first liquefied gas fuel, because this composition can change during operation on the one hand, and because on the other hand these changes in the composition have a negative influence on the combustion process concerning a complete, proper combustion of the fuel, an blow-in time of the particularly first liquefied gas fuel being dependent on the calorific value or the gas-mixture-characteristic value, i.e. feedback control of the blow-in time using the determined calorific value or the determined gas-mixture-characteristic value being dependent on the composition of the gas mixture, enables counteracting or even eliminating this negative influence.

By arranging the apparatus so that the determined blow-in time of the liquefied gas fuel depends on a determined calorific value or determined gas mixture-characteristic-value, particularly reliable bivalent or trivalent fuel mode operation based on one or more liquefied gas fuels can thus be enabled. Aiming at almost complete combustion, combustion of the bivalent or trivalent fuel in the engine can be regulated in such targeted manner that even a gas start is possible, i.e. to start the engine in liquefied gas operation, especially without burning liquid fuel, also possible at low outside temperatures around zero, i.e. 0° C.

A further aspect of the invention concerns an add-on control unit or an apparatus comprising an add-on control unit for determining a blow-in time of a particularly first liquefied gas fuel and/or an amount of an particularly second liquefied gas fuel to be supplied to a cylinder of an engine for operating the engine in a bivalent or trivalent fuel mode, wherein the apparatus or add-on control unit each having an interface to an intake-manifold-pressure-sensor for determining an engine load in a gasoline engine, a rail-pressure-sensor and/or intake-manifold-pressure-sensor for determining an engine load in a diesel engine, a lambda-offset-module for performing a lambda offset adjustment, a gas-mixture-analysis-module for determining a calorific value or gas-mixture-characteristic value dependent on a composition of a gas mixture of the liquefied gas fuel for shifting a blow-in-time-look-up-table towards rich or lean, a safety-module for protecting the engine from excessively high combustion temperatures, at least one gas blow-in-valve (gas injection valve) for releasing the gas mixture, at least one injection device for injecting a liquid fuel such as gasoline or diesel, an $H_2$-module for delivering the amount of hydrogen to be supplied as the first liquefied gas fuel to the cylinder of the engine, a vehicle OBD system and/or an engine control unit for monovalent fuel mode operation of the engine with liquid fuel—such as diesel, biodiesel or gasoline.

A bivalent or trivalent fuel mode operation can thus be achieved particularly reliably and with low pollutant emissions. Particularly, the combination of the lambda-module interface and the gas-mixture-analysis-module interface enables particularly complete combustion, and with the additional combination with the $H_2$-module interface a particularly low pollutant emissions can be achieved, wherein these combination effects are synergetically greater than the sum of the effects that can be achieved separately with the aforementioned module interfaces. This also applies in a similar way to the other above mentioned interfaces.

A further aspect of the invention concerns an apparatus with an add-on control unit for determining a blow-in time for a particularly first liquefied gas fuel and/or an amount of a particularly second liquefied gas fuel to be supplied to a cylinder of an engine for operating the engine in a bivalent or trivalent fuel mode, wherein the apparatus comprises a lambda-offset module for conducting a lambda-offset adjustment, a gas-mixture-analysis-module for determining a calorific value or gas-mixture-characteristic value dependent on a composition of a gas mixture of the liquefied gas fuel for shifting a blow-in-time-look-up-table towards rich or lean, a safety-module for protecting the engine from excessively high combustion temperatures, at least one gas blow-in-valve for releasing the gas mixture and/or an $H_2$-module for delivering the amount of hydrogen as the first liquefied gas fuel to be supplied to the cylinder of the engine.

Bivalent or trivalent fuel mode operation can thus be achieved particularly reliably and with low pollutant emissions. Particularly, the combination of the lambda-module and the gas-mixture-analysis-module enables particularly complete combustion, and having the additional combination with the $H_2$-module particularly low pollutant emissions, wherein these combination effects are synergetically greater than the sum of the effects that can be achieved separately with the aforementioned modules. This also applies in a similar way to the other components that can be connected via above mentioned interfaces.

Another aspect of the invention concerns a gas-mixture-analysis-module for the above described apparatus or for connecting to the above described add-on control unit, wherein the gas-mixture-analysis-module is designed such that the density of the gas mixture can be determined from the temperature and pressure of the gas mixture of the liquefied gas fuel and/or, dependent on the current composition of the gas mixture, the calorific value of the gas mixture or the gas-mixture-characteristic value of the gas mixture can be determined by using a gas-mixture-analysis-look-up-table based on the gas conductivity, the temperature and the density or based on the gas conductivity, the temperature and the pressure of the gas mixture. The entire disclosure of this application applies not only to the apparatus according to the invention and the add-on control unit according to the invention, but also to the gas-mixture-analysis-module according to the invention provided that the respective disclosure is directly or indirectly related to the gas-mixture-analysis-module.

Another aspect of the invention concerns a gas-start-system for the above described apparatus or for connection to the add-on control unit described above, wherein the gas-start-system is arranged such that when the engine is started in a pure liquefied gas mode, only the gaseous phase of the gas mixture of the liquefied gas fuel is withdrawn from a gas tank for blow-in into the cylinder of the engine. The entire disclosure of this application applies not only to the apparatus according to the invention and the add-on control unit according to the invention, but also to the gas-start-system according to the invention provided that the respective disclosure is directly or indirectly related to the gas-start-system.

Pure liquefied gas mode means operating the engine exclusively with a liquefied gas fuel or a liquefied gas fuel and hydrogen.

Another aspect of the invention concerns a method for determining a blow-in time of a first liquefied gas fuel in form of a gas mixture, in particular autogas (LPG), natural gas (CNG), liquefied natural gas (LNG), biogas, and/or determining an amount of a second liquefied gas fuel, in particular hydrogen, to be supplied to a cylinder (19a) of an engine (19) preferably continuously, wherein in particular the apparatus or the add-on control unit of one of the preceding aspects of the invention are used, wherein in particular, a calorific value or a gas-mixture-characteristic value is determined based on a gas conductivity, a temperature and a pressure of the gas mixture, in particular, based on a lambda value and/or a NOx value, an offset-lambda value and/or offset-NOx value that depend on the first liquefied gas fuel are determined, preferably specific for a lambda sensor and/or NOx sensor used, in particular, based on the calorific value or gas-mixture-characteristic value, a gas-mixture-adjustment-factor is determined, in particular, the blow-in time determined based on the engine load and/or the engine speed using a blow-in-look-up-table which has been shifted towards rich or lean using the gas-mixture-adjustment-factor, the offset-lambda value and/or offset-NOx value, and/or in particular, the amount of the second liquefied gas fuel to be supplied is determined using a gas-amount-look-up-table based on the engine load and/or the engine speed, wherein in particular, the blow-in time and/or the amount to be supplied are increased or reduced particularly stepwise based on a knock signal.

Another aspect of the invention concerns the use of a gaseous phase of liquefied gas fuel present in a gas tank, particularly LPG or LNG, for blow-in into an engine for driving a vehicle, particularly for a gas start of the vehicle.

The meaning of gas start is described below.

Particularly, only the gaseous phase of the liquefied gas fuel present in the gas tank serves as the sole fuel for the engine to drive the vehicle.

Particularly, only the gaseous phase of the liquefied gas fuel present in the gas tank and hydrogen serve as the sole fuels for the engine to drive the vehicle.

In the following, the invention, thus the aspects of the invention, is further explained and described on the basis of preferred exemplary embodiments shown in the figures.

Figure 2:
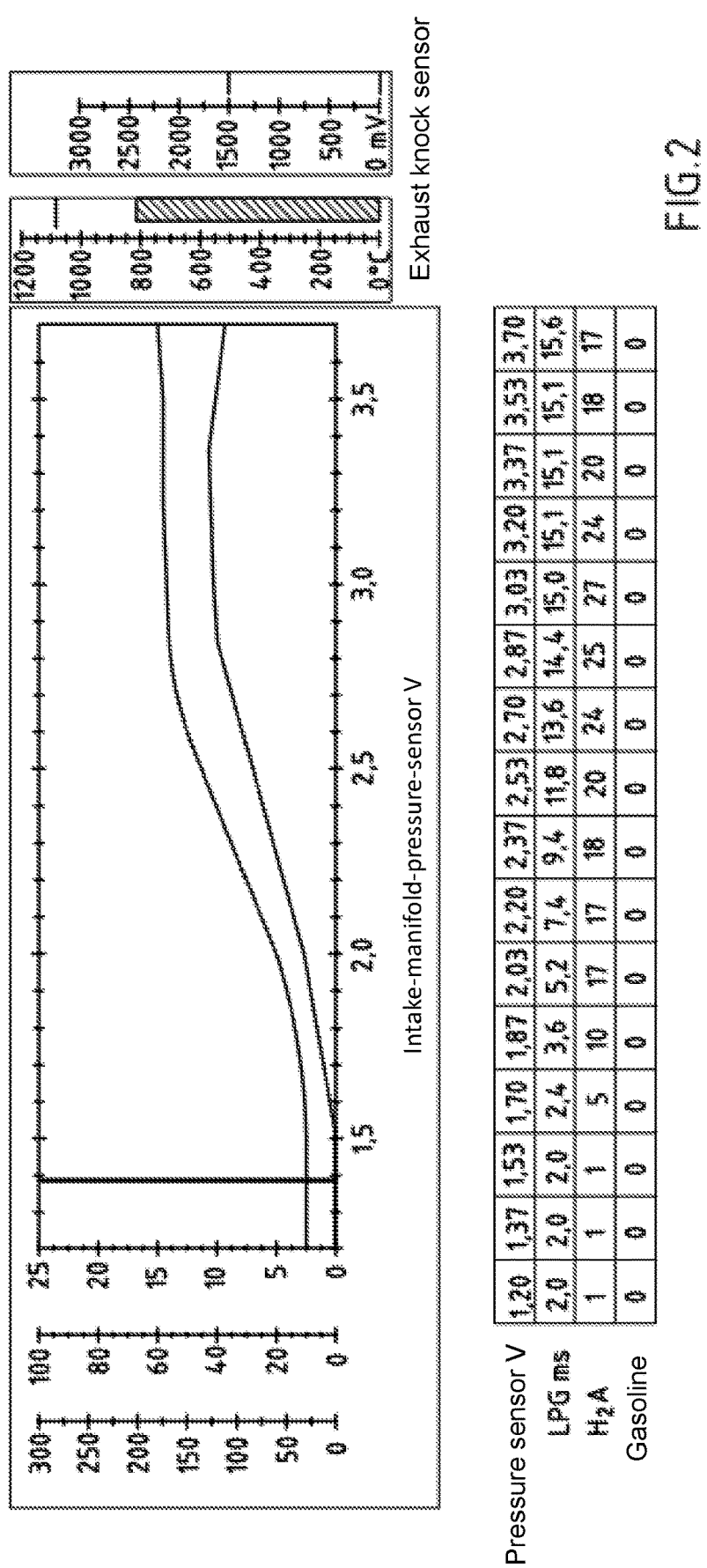
FIG. 2 shows a determined gas blow-in time for LPG and a determined amount of hydrogen to be supplied through the add-on control unit using a gas-blow-in-look-up-table for a bivalent fuel mode operation of a gasoline engine in which in a liquefied gas mode no gasoline injection takes place.
Figure 4:
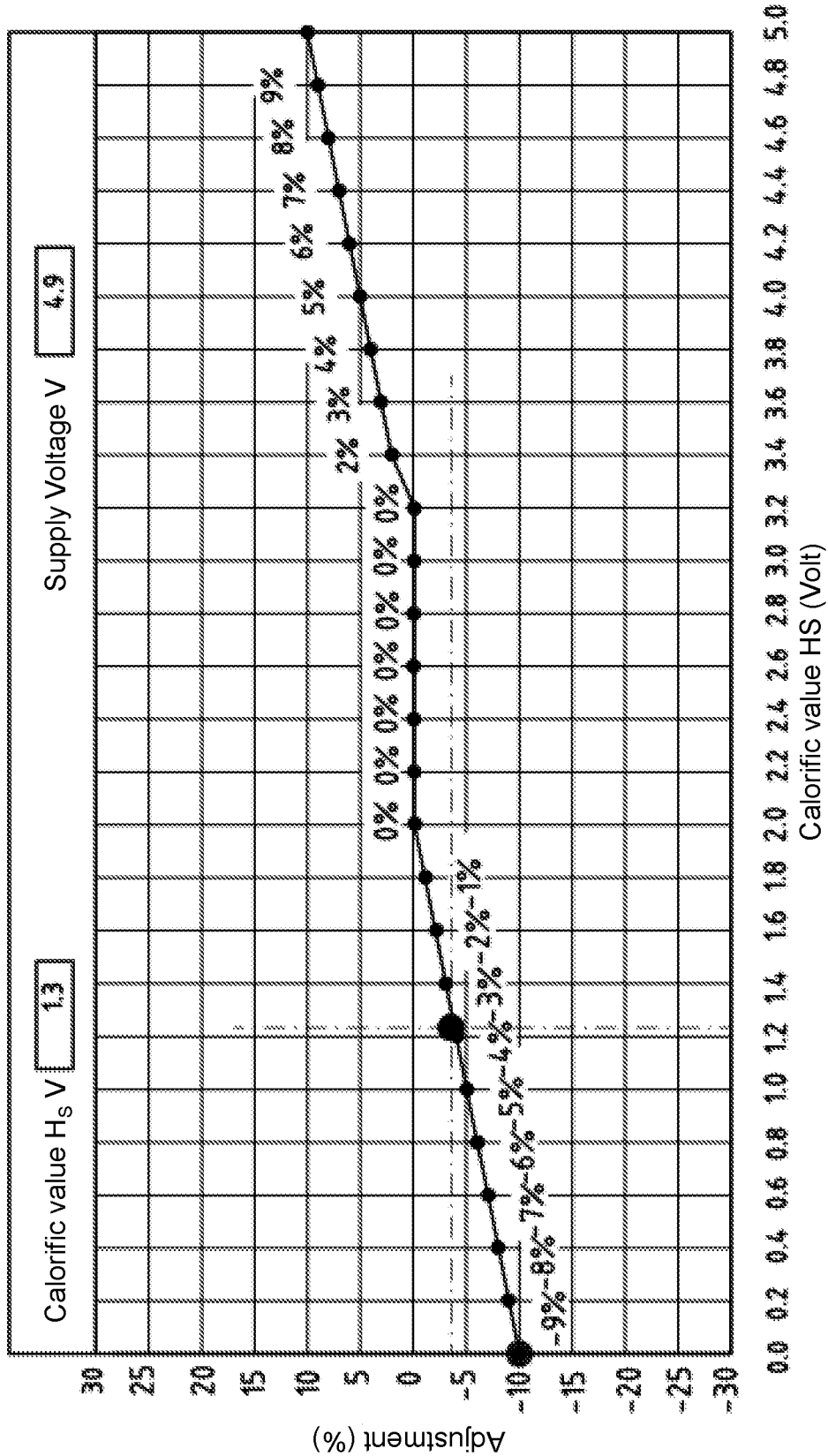
FIG. 4 shows a gas-mixture-regulating-look-up-table of the add-on control unit for the gas-blow-in-look-up-table of FIG. 2.
Figure 5:
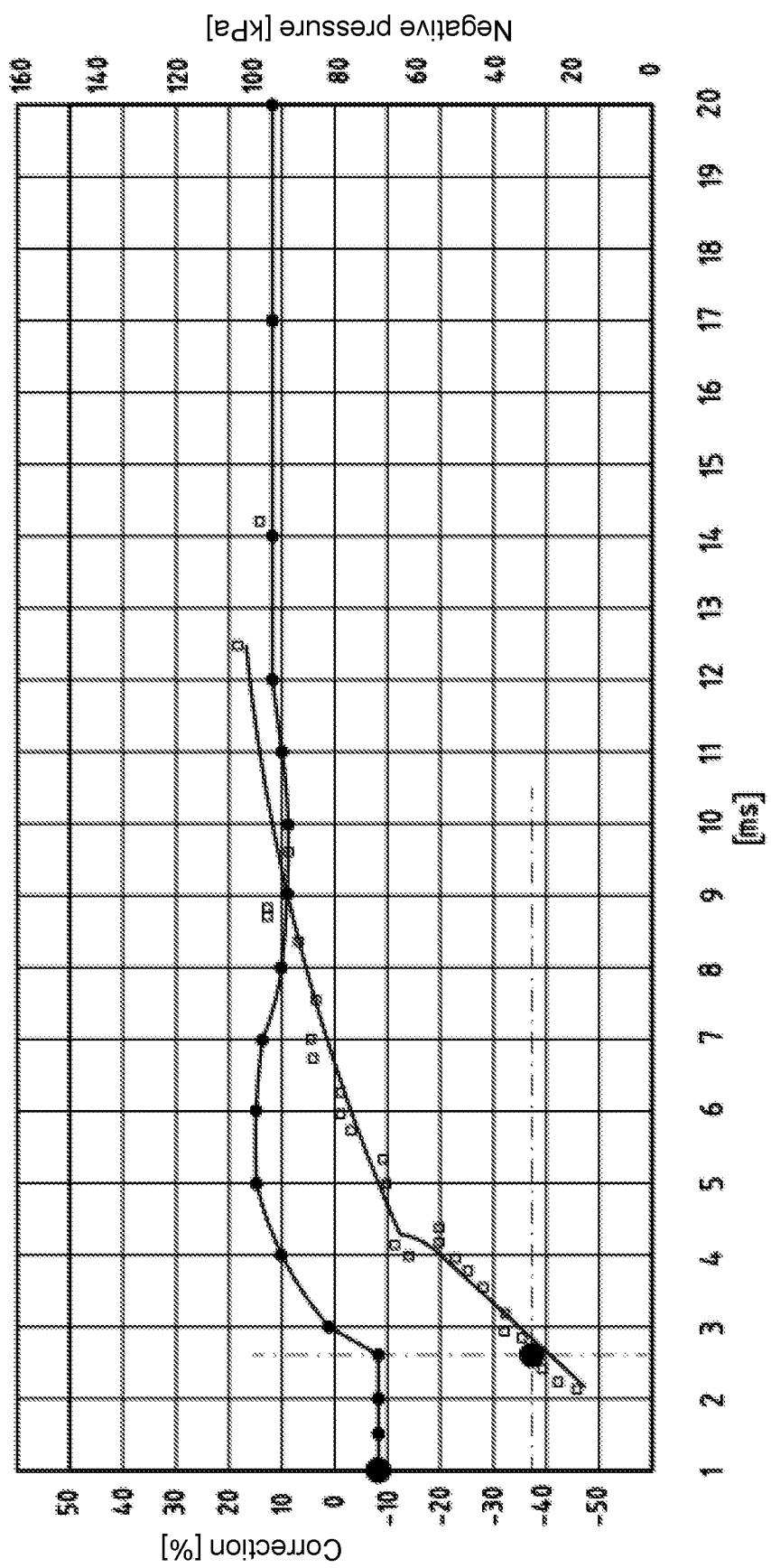
Figure 6:
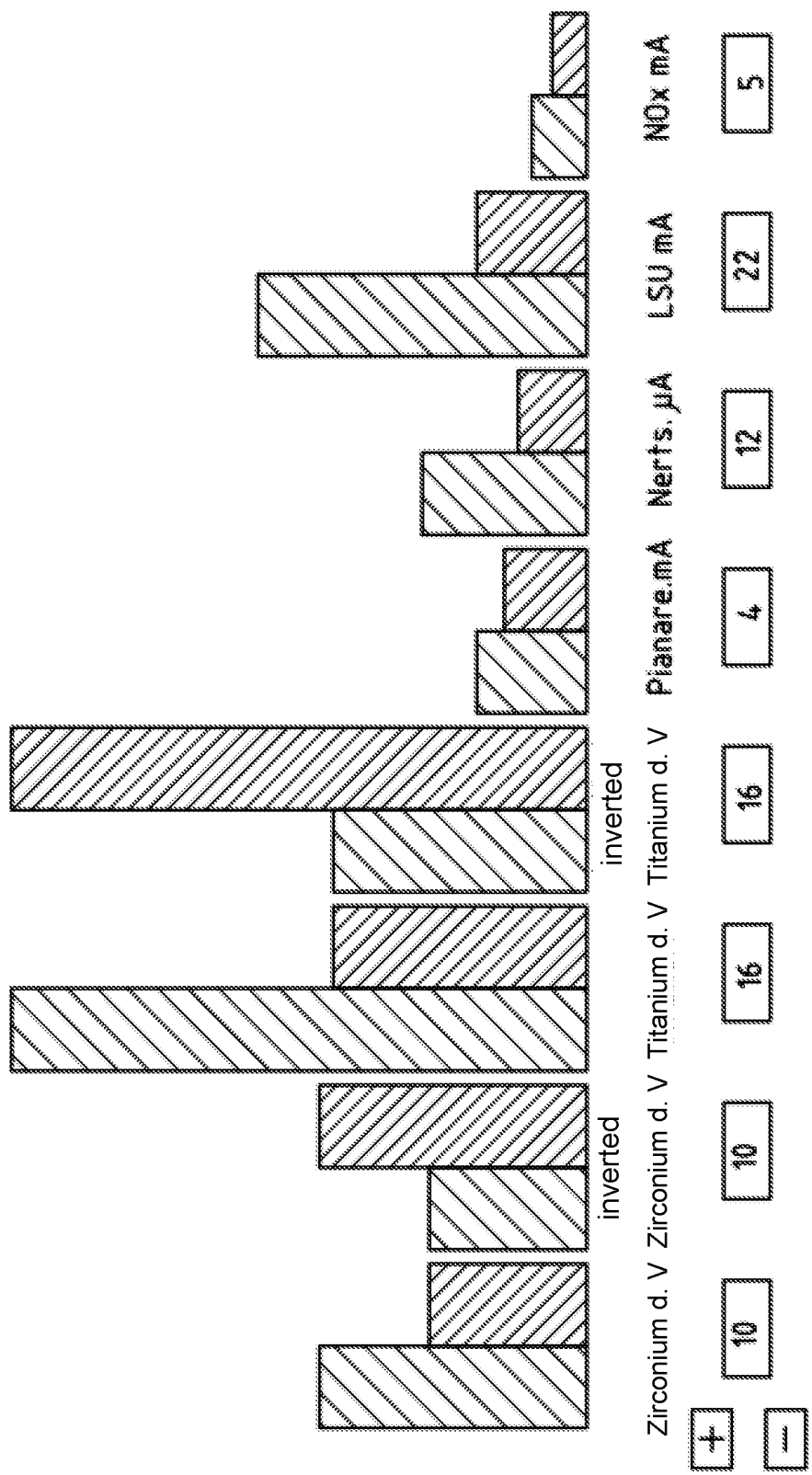

FIG. 5 shows a real gas blow-in characteristic curve as an extract from the gas-blow-in-look-up-table on which FIG. 2 is based, taking into account the gas-mixture-regulating-look-up-table of FIG. 4 and the offset-lambda value of FIG. 6, wherein the gas blow-in characteristic curve with plotted correction factor in [%] is compared with an engine load characteristic curve (top left) in gasoline mode operation with plotted negative pressure in [kPa] over the injection time in [ms].

FIG. 6 shows a lambda-offset adjustment and NOx adjustment by offset factors for different lambda sensors and NOx sensors for the gas-blow-in-look-up-table of FIG. 2, wherein the signal values are compared before the adjustment (in each case left bar) and after the adjustment (in each case right bar).

Figure 7:
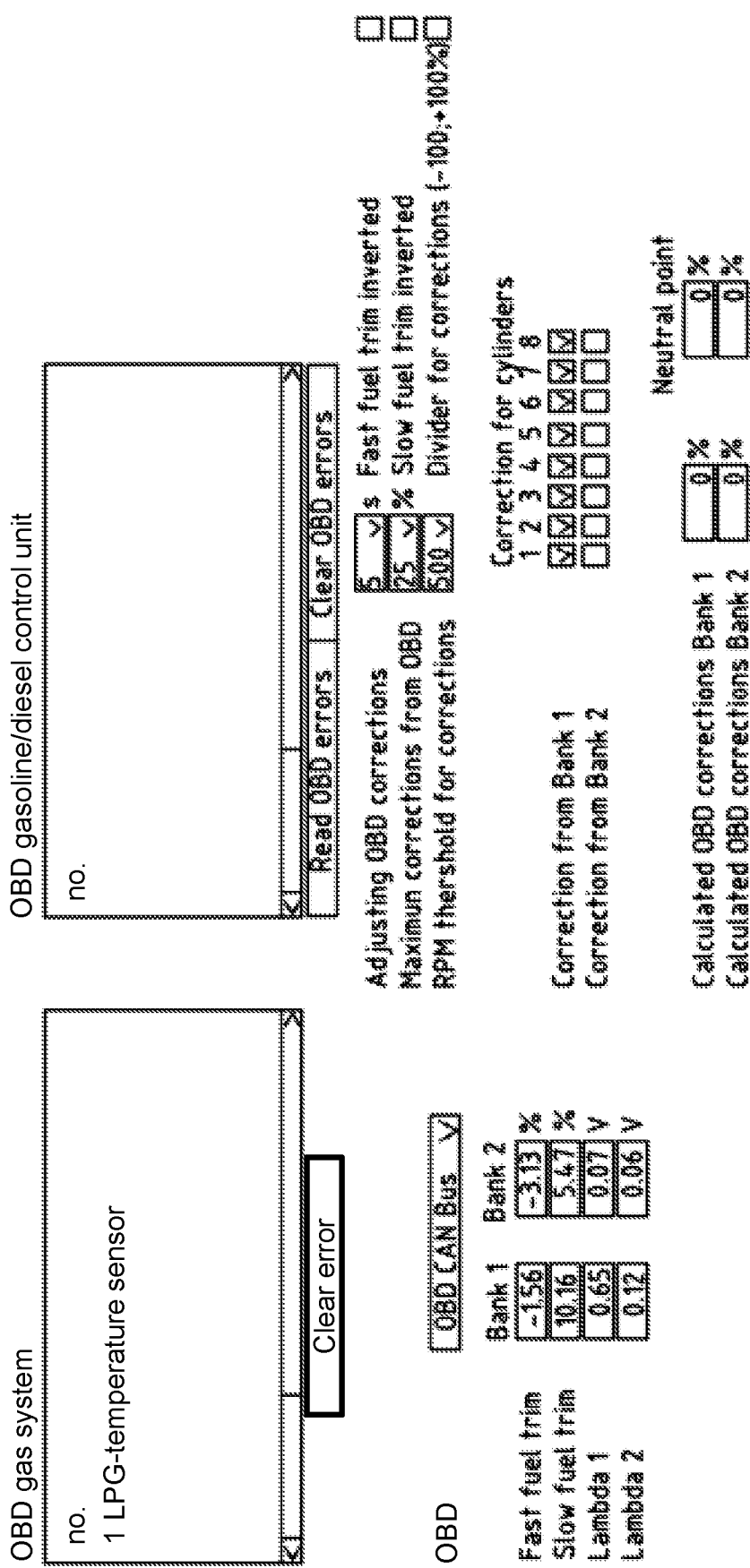

FIG. 7 shows an on-board diagnostics (OBD) control of the add-on control unit 18 in master mode independent of the engine control unit 20 operated as a slave.

Figure 8:
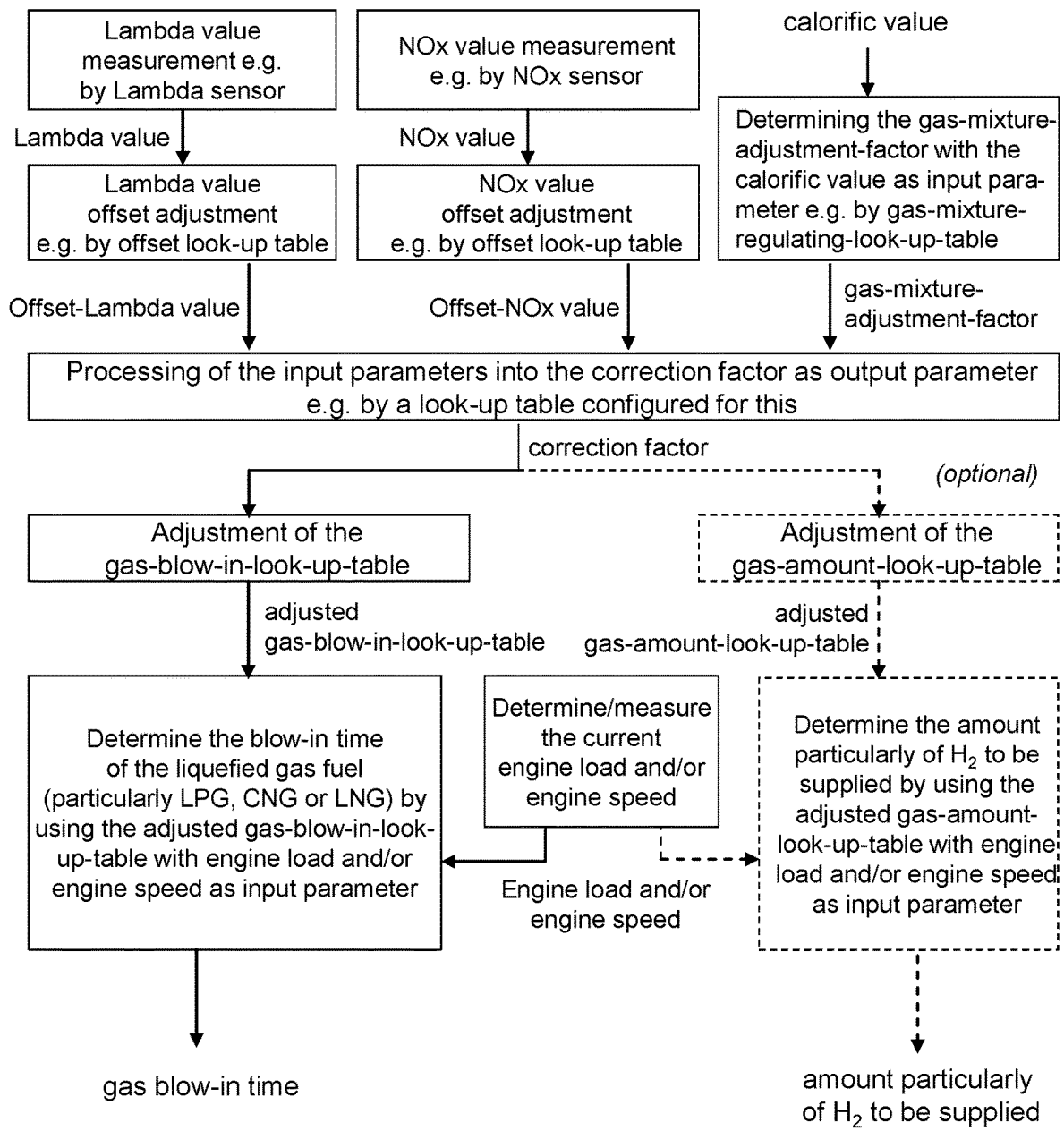
Figure 9:
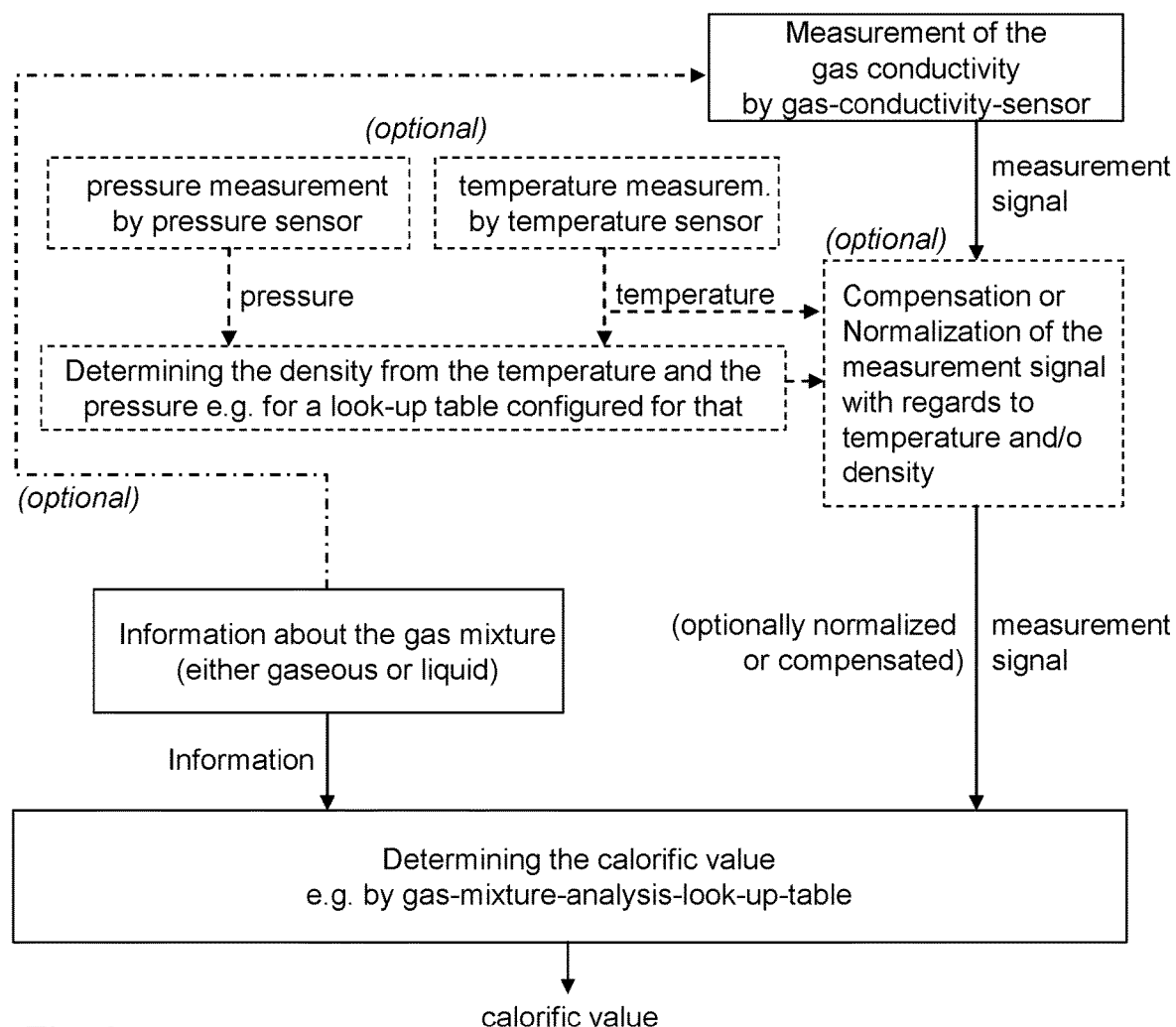

FIGS. 8 and 9 show exemplary flow diagrams for processes described below.

Figure 10:
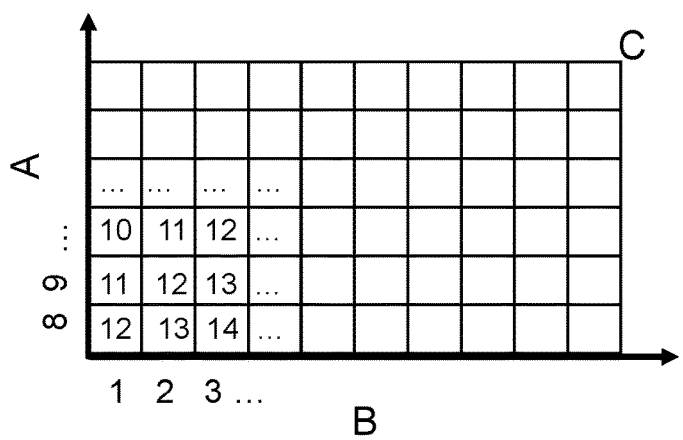

FIG. 10 shows an exemplary look-up table and illustrates the determination of an output parameter C based on input parameters A and B.

In one embodiment, the apparatus is arranged for a particularly first liquefied gas fuel in form of a gas mixture 2, 21 such that the calorific value and/or the gas-mixture-characteristic value can be determined in dependency of a current composition of the gas mixture 2, 21.

Gas mixture means a mixture comprising or consisting of at least two different gases. For example, LPG consists of butane and propane, whereby an exemplary current composition can be 70% butane and 30% propane. However, the gas mixture may also contain three, four or more different gases, whereby it is possible to take into account the proportions of these other gases in the gas mixture when determining the calorific value or gas-mixture-characteristic value, or to neglect them. The proportions are determined preferably in volume percent, alternatively in weight percent.

By determining the calorific value and/or the gas-mixture-characteristic value in dependency of a current composition of the gas mixture 2, 21, it is enabled that during controlling (regulating) the combustion process by the apparatus or the add-on control unit 18, it can be taken into account a change in the composition during operation, thus changing gas proportions such as 70% butane and 30% propane to 60% butane and 40% propane as a result of one of the following: vehicle refueling and/or temperature influences, a changed filling level of the gas tank 3 or by starting the engine. A proper combustion process can thus be achieved even at fluctuating or low outside temperatures and a gas start is made possible.

In one embodiment, the apparatus comprises a gas-conductivity-sensor 8 for measuring an electrical conductivity of the gas mixture 2, 21 particularly in the liquid phase 2 and/or the gaseous phase 21 of the liquefied gas fuel.

Gas conductivity or electrical conductivity of the gas mixture 2, 21 means the ability of the gas mixture 2, 21 to conduct electrical current.

By providing a gas-conductivity-sensor 8 for measuring the electrical conductivity of the gas mixture 2, 21, the prerequisite for particularly accurate determination of the current calorific value and/or of the gas-mixture-characteristic value, optionally also of the current composition, of the gas mixture 2, 21 can be created.

In particular, the apparatus is arranged such that the calorific value and/or the gas-mixture-characteristic value can be determined based on the measured electrical conductivity.

This enables particularly accurate determination of the current calorific value and/or the gas-mixture-characteristic value for very reliable regulation of the combustion process.

In one embodiment, the gas-conductivity-sensor 8 comprises an anode and a cathode and/or the gas-conductivity-sensor 8 is arranged such that for measuring the electrical conductivity a constant voltage can be applied between the anode and cathode and a measuring current can be fed through the gas mixture 2, 21 in the liquid phase 2 or in the gaseous phase 21.

A very reliable measurement of the electrical conductivity with a particularly simple and inexpensive sensor is thereby enabled.

In one embodiment, the apparatus comprising a temperature sensor 1 for measuring the temperature of the gas mixture 2, 21 of the liquefied gas fuel and/or a pressure sensor 9 for measuring the pressure of the gas mixture 2, 21 of the liquefied gas fuel and/or the apparatus is arranged such that the calorific value or the gas-mixture-characteristic value can be determined based on the measured temperature and/or the measured pressure. Particularly, temperature sensor 1 measures the temperature and/or pressure sensor 9 measures the pressure of the gas mixture 2, 21 on the way from a gas tank 3 to an evaporator and/or pressure-regulator 11.

By measuring the temperature and/or the pressure of the gas mixture 2, 21 particularly on the way from a gas tank 3 to an evaporator and/or pressure-regulator 11, a normalization of the measured gas conductivity to a defined temperature and/or to a defined pressure can be obtained in order to obtain a value of the gas conductivity independent of the temperature and/or the pressure, whereby the evaporator basically fulfils its function of evaporation only with a gas mixture in the liquid phase 2 and thus usually only the pressure-regulator 11 acts properly on the gas mixture in the gaseous phase 21.

Preferably, the density of the gas mixture 2, 21 is determined using the temperature and pressure, and the measured gas conductivity is normalized to a defined density in order to obtain a value of the gas conductivity independent of the density.

Particularly preferably, the density of the gas mixture 2, 21 is determined from the temperature and the pressure and, together with the temperature, a temperature and density normalized input parameter is determined for determining the calorific value or the gas-mixture-characteristic value.

A particularly reliable determination of the calorific value or the gas-mixture-characteristic value by means of a comparatively simply structured gas-mixture-analysis-characteristic-look-up-table can thus be enabled.

In one embodiment, the apparatus is connected to a gas-mixture-analysis-module 7 which is arranged such that the density of the gas mixture 2, 21 can be determined from the temperature and the pressure of the gas mixture 2, 21, and/or wherein the calorific value and/or the gas-mixture-characteristic value can be determined in dependency of the current composition of the gas mixture 2, 21 based on the gas conductivity, the temperature and the density of the gas mixture 2, 21 by using a gas-mixture-analysis-look-up-table. In particular, the add-on control unit 18 is connected to the gas-mixture-analysis-module 7 via an interface. Basically, the apparatus or the add-on control unit 18 can also have the gas-mixture-analysis-module.

A look-up-table, thus gas-mixture-analysis-look-up-table, gas-mixture-regulating-look-up-table, gas-blow-in-look-up-table, gas-amount-look-up-table, diesel-look-up-table, gasoline-look-up-table, offset-look-up-table, is basically a table or matrix with preset or stored values. The values are usually digital and stored particularly on a storage medium. Particularly, these values do not change during operation, but are transferred to the storage medium or changed and stored preferably only as part of production or configuration.

Such a look-up-table usually has at least two axes.

FIG. 4 shows a gas-mixture-regulating-look-up-table with exactly two axes for determining a gas-mixture-adjustment-factor using the calorific value $H_S$, with the first axis representing the calorific value $H_S$ and the second axis representing the gas-mixture-adjustment-factor. The gas-mixture-regulating-look-up-table therefore contains a table with only one row and a large number of columns or alternatively only one column and a large number of rows, where each row and column is usually filled with numerical values. As FIG. 4 shows, a two-dimensional look-up-table can be displayed with X and Y axes as a curve.

An example of a look-up-table with exactly three axes is the gas-amount-look-up-table, which is explained in detail below to illustrate the meaning of a look-up-table.

Accordingly, a look-up-table can have four or more axes, whereby more than two input parameters can be assigned to one output parameter.

Particularly, the gas-mixture-analysis-look-up-table has exactly four axes with the input parameter of gas conductivity, temperature and density of the gas mixture 2, 21 preferably immediately after leaving the gas tank 3 on the way towards the blow-in-valve 17.

The gas-mixture-analysis-look-up-table enables a particularly fast and reliable determination of the calorific value or the gas-mixture-characteristic value. Furthermore, subsequent calibration, i.e. re-calibration of the numerical values of the gas-mixture-analysis-look-up-table, can improve precision very easily also after the apparatus has been manufactured.

In one embodiment, the apparatus, particularly an add-on-module 18, comprises a gas-mixture-regulating-look-up-table which is arranged such that, based on the determined calorific value or the determined gas-mixture-characteristic value, a gas-mixture-adjustment-factor can be determined, on which the determined blow-in time depends.

The gas-mixture-regulating-look-up-table is shown in FIG. 4 and has already been explained above.

The thereby determined gas-mixture-adjustment-factor serves as a correction variable for determining the blow-in time, particularly using the blow-in-look-up-table preferably of the add-on control unit 18. A very effective regulation of the combustion process for maintaining a combustion as complete as possible is thereby enabled.

The difference between an input parameter and a correction variable is described in more detail below.

In one embodiment, the apparatus is connected to a lambda-offset-module 28 in order to obtain, based on a measured lambda value and/or measured NOx value, an offset-lambda value and/or offset-NOx value adapted to the liquefied gas fuel, wherein the blow-in time is dependent on the offset-lambda value and/or offset-NOx value. Particularly, the add-on control unit 18 is connected to the lambda-offset-module 28 via an interface.

Particularly, the lambda-offset-module 28 has a lambda sensor 45 and/or a NOx sensor 46, or is connected to the lambda sensor 45 and/or a NOx sensor 46 via an interface. Basically, the apparatus or add-on control unit 18 can also have the offset-look-up-table.

Particularly, the lambda-offset-module 28 has an offset-look-up-table which assigns a measured lambda value as input parameter to an offset-lambda value as output parameter in dependency of the lambda sensor 45 used.

Particularly, the offset-look-up-table is furthermore arranged such that a measured NOx value as input parameter can be assigned to an offset-NOx value as output parameter in dependency of the NOx sensor 46 used.

FIG. 6 compares lambda values and the corresponding offset-lambda values as well as NOx values and the corresponding offset-NOx values after processing using the offset-look-up-table for several different lambda sensors 45 and NOx sensors 46.

Particularly, only the offset-lambda values and/or offset-NOx values are transmitted to the engine control unit 20 to avoid error messages and incorrect regulation of an injection time for gasoline or diesel.

The thereby determined offset-lambda value and/or offset-NOx value serve as input parameters for determining the blow-in time, especially using the blow-in-look-up-table, preferably of the add-on control unit 18. A very effective regulation of the combustion process to achieve a combustion as complete as possible is enabled.

In one embodiment, the apparatus, particularly the add-on-module 18, comprises a gas-blow-in-look-up-table for determining the blow-in time preferably of LPG or CNG in dependency of the current engine load and/or the current engine (rotational) speed, and/or the gas-blow-in-look-up-table allows a shift towards rich or lean in dependency of the gas-mixture-adjustment-factor and/or a shift towards rich or lean in dependency of the offset-lambda value.

The meaning of shifting a look-up-table is described below.

A very effective regulation of the combustion process for obtaining a combustion as complete as possible is thereby enabled.

In one embodiment, the apparatus, particularly the add-on-module 18, comprises a gas-amount-look-up-table for determining the amount particularly of the second liquefied gas fuel to be supplied, preferably of hydrogen, in dependency of the current engine load and/or the current engine speed.

The load-dependent supply of particularly hydrogen enables the consumption of particularly the second liquefied gas fuel while still having low pollutant emissions.

Particularly, the gas-amount-look-up-table has exactly three axes in order to obtain a numerical value based on the engine load, i.e. the load value, and the (rotational) speed, which is transmitted as digital or analog signal from the hydrogen cell 38 to release an amount of hydrogen that correlates with the numerical value. The higher the numerical value, the more hydrogen is continuously released and supplied to the cylinder.

The gas-amount-look-up-table with exactly three axes can be displayed in the form of a table with the numerical values, wherein in each column a speed in revolutions per minute, e.g. column 1: "1000 rpm", column 2: "2000 rpm" etc. as column headings, and wherein in each line, the load value in bar or volts, as corresponding analog signal quantity, are listed e.g. of the rail-pressure-sensor 44 for a diesel engine, e.g. line 1: "2 V", line 2: "2.5 V", line 3: "3 V", etc. as line headings. The table cells below the column headings and next to the row headings are filled with numerical values which are used to control the hydrogen cell 38. Each numerical value thus represents a parameter for the amount of hydrogen to be supplied.

Such a look-up table with three axes could only be displayed in a single diagram with a large number of curves arranged together.

A look-up table can be arranged such that the look-up table allows the look-up table to be shifted along an axis by a correction factor. Simply said, in the event of such shifting for example in the above gasoline-look-up-table example, the line headings are moved up or down by the correction factor or the line headings are increased or reduced by the correction factor by multiplication, division, addition or subtraction. As shown in FIG. 5, this allows an exemplary curve of the blow-in-time-look-up-table to be shifted along the X-axis and/or Y-axis for a certain speed or to modify the curve profile.

In FIG. 5, the curve with starting point at 1 on the X-axis and −10 on the Y-axis represents the engine load characteristic as negative pressure in [kPa] over the injection time in [ms], recorded and stored by a drive in gasoline mode. The other curve shows for an injection of LPG corrected curve of a correction factor in [%] over the blow-in time in [ms]. The corrected curve illustrates a shift of the engine load characteristic from the gasoline mode for operating in liquefied gas mode under the influence of the correction factors offset-lambda value, offset-NOx value and gas-mixture-adjustment-factor.

In one embodiment, the apparatus is connected to an $H_2$-module 28 for particularly continuously supplying the amount of hydrogen to be supplied to the cylinder, and/or the $H_2$-module (28) comprises a knock sensor 39 and/or can transmit a knock signal to the apparatus in order to preferably stepwise reduce and/or, in case of absence of a knock signal over a predetermined time period or predetermined number of work cycles, to preferably stepwise increase the amount to be supplied and/or the blow-in time. Particularly, the add-on control unit 18 is connected to the $H_2$-module 28 via an interface. Basically, the apparatus or add-on control unit 18 can also comprise the $H_2$-module 28.

The detection of knocking during the combustion process and the resulting particularly stepwise control of the blow-in time and amount to be supplied allows both the particularly continuously supplied hydrogen and the particularly sequentially blown-in LPG or CNG to be used for proper combustion in bivalent or trivalent fuel mode.

In one embodiment, the apparatus, particularly the add-on control unit 18, has an integrated on-board diagnosis (OBD) control that can communicate with the vehicle OBD system via an OBD interface and/or is configured for master mode operation in the liquefied gas mode.

In one embodiment, the apparatus is the add-on control unit 18 or a particularly retrofittable add-on control unit 18. Preferably, the apparatus is retrofittable, i.e. designed for allowing later installation into a vehicle with an engine, thus after production of the vehicle for monovalent operation with liquid fuel.

In one embodiment, the apparatus or add-on control unit 18 comprises an interface to a Gas-start-system for starting the engine 19 in a pure liquefied gas mode when gas start is programmed. The interface particularly comprises a control line 50 for remote control of a supply valve 51, a control line 35 for a second remotely-controlled shut-off valve 33 and/or a control line 50 for a first remotely-controlled shut-off valve 10.

Figure 3:
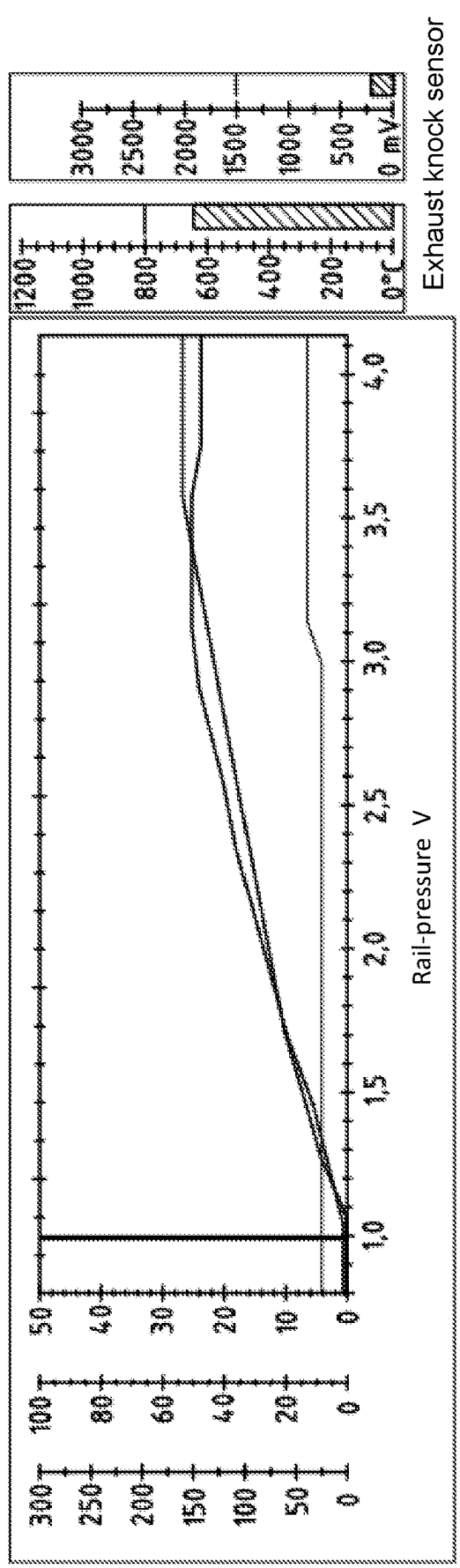
FIG. 3 shows a determined gas blow-in time for LPG and amount of hydrogen to be supplied as well as an injection time for diesel determined by the add-on control unit using a gas-blow-in-look-up-table for trivalent fuel mode operation of a diesel engine.

FIGS. 2 and 3 show the resulting blow-in times for LPG, $H_2$ and gasoline or diesel, wherein no gasoline is burned in gasoline operation. In diesel operation and only in petrol-direct-injection-engines, a proportion of liquid fuel is delivered to the cylinders for cooling purposes for a bivalent or trivalent fuel mode operation.

The gas-start-system according to an above described further aspect of the invention has, in one embodiment, a gas-extraction-connection preferably with a valve 31 to feed the gaseous phase 21 of the gas mixture 2, 21 from the gas tank 3, particularly via a gas line 32, to a second remotely-controlled shut-off valve 33.

In a further embodiment of the gas-start-system, the gas-start-system has an analogue or digital control line 35 for connecting to the above described apparatus or add-on control unit 18.

In a further embodiment of the gas-start-system, the gas-start-system has an analogue or digital control line 35 for the second remotely-controlled shut-off valve 33 for feeding or shutting off the gaseous phase 21 of the gas mixture 2, 21 via the gas line 32 to the liquefied gas line 6.

In a further embodiment of the gas-start-system, the gas-start-system has a first remotely-controlled shut-off valve 10, remotely-controllable via the analog or digital control line 36, for closing or opening a connection from the liquefied gas line 6 to an evaporator and/or pressure-regulator 11.

In a further embodiment of the gas-start-system, the gas-start-system has a supply valve 51, which can be remotely-controlled via an analogue or digital control line 50, for shutting off or allow inflow of the liquid phase 21 of the gas mixture 2, 21 of the gas tank 3 into the liquefied gas line 6.

The term "gas-start-system" can alternatively named "device for a gas start" as a synonym.

The evaporator or pressure-regulator 11 now receives the gas from the gaseous phase 21 via the second remotely-controlled shut-off valve 33 and/or via the first remotely-controlled shut-off valve 10 and operates nothing but as pressure-regulator 11.

Another aspect of the invention concerns a method for controlling (regulating) a gas start with the Gas-start-system described above and/or with the apparatus described above, wherein, when gas start is programmed,
 particularly via control line 50, supply valve 51 is kept closed so that no gas mixture 2, 21 in the liquid phase 2 can reach the evaporator and/or pressure-regulator 11 or an blow-in-valve 17, and/or
 particularly via the control line 35, the second shut-off valve 33 is opened to allow inflow of the gaseous phase 21 of the gas mixture 2, 21 from the gas tank 3, preferably via the gas line 32, into the liquefied gas line 6 to the evaporator and/or pressure-regulator 11.

In a further embodiment of the method for controlling a gas start, it is provided that when the temperature of the cooling water of the engine 19, preferably measured by water temperature sensor 37, reaches switch-temperature, particularly stored in the add-on control unit 18, the second remotely-controlled shut-off valve 33 closes and the remotely-controlled supply valve 51 opens so that the inflow of the gaseous phase 21 of the gas mixture 2, 21 to the evaporator and/or pressure-regulator 11 is blocked and instead the liquid phase 2 of the gas mixture 2, 21 is supplied from the pressure tank 3 to the evaporator and/or pressure-regulator 11.

Figure 1:
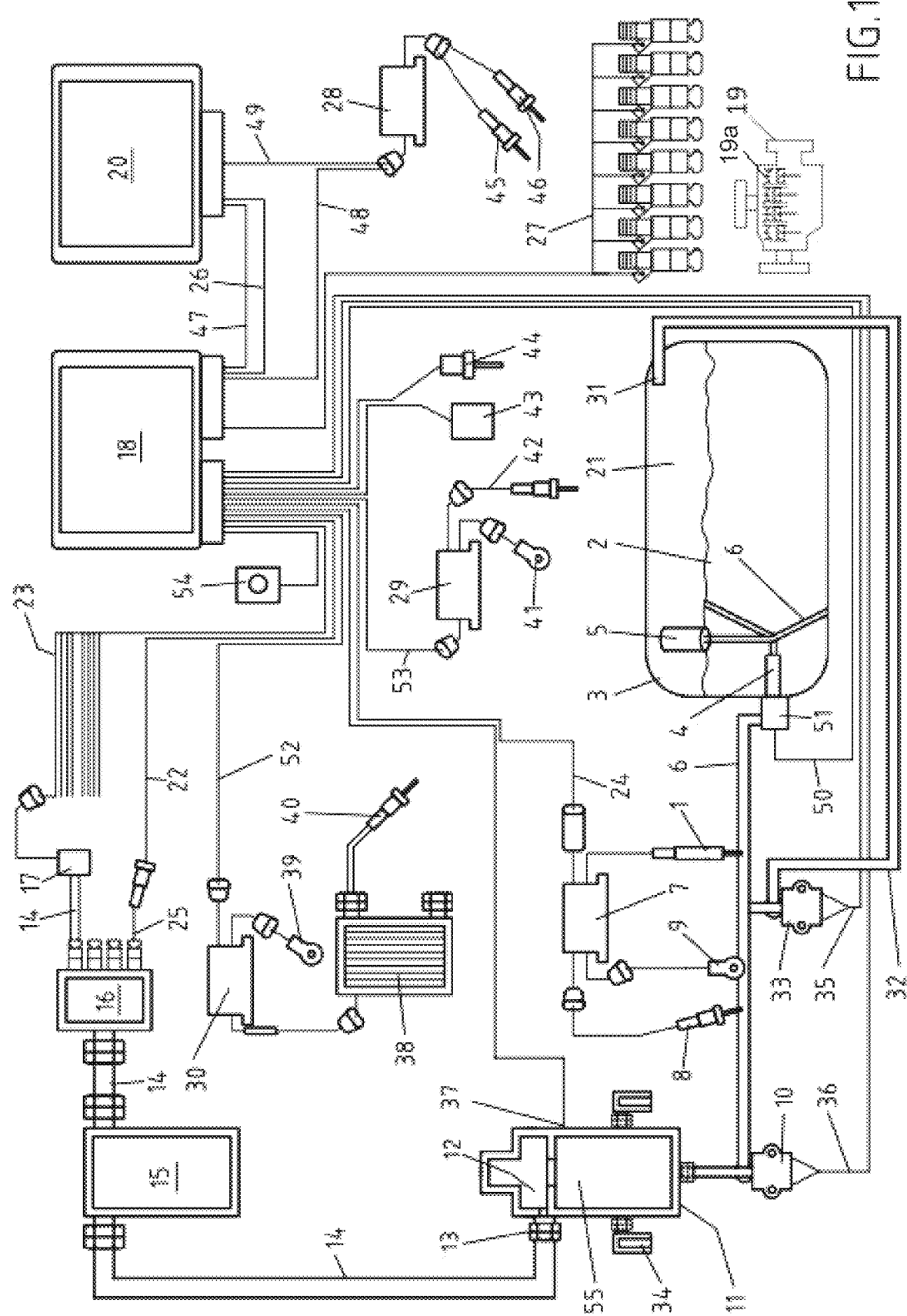
FIG. 1 shows an overview of a system comprising the apparatus or add-on control unit, respectively, for bivalent or trivalent mode operation of an engine 19 to drive a vehicle.

FIG. 1 shows an overview of an exemplary system for bivalent or trivalent fuel mode operation, i.e. particularly for operation with a diesel or gasoline fuel, a liquefied fuel and/or hydrogen, comprising an engine control unit 20, installed particularly by the vehicle manufacturer, and a preferably retrofittable add-on control unit 18 in master-slave operation, the engine control unit 20 corresponding to the slave and the add-on control unit 18 corresponding to the master.

The engine 19 can preferably be started in liquefied gas mode by using the add-on control unit according to the invention, which is hereinafter called gas start, i.e. not in gasoline or diesel mode.

In one embodiment, the gaseous phase 21 of the gas mixture 2, 21 is, particularly solely, fed to an blow-in-valve 17 as fuel for the engine 19 for a gas start. A gas start can thus be conducted successfully at low outside temperatures.

A gas mixture 2, 21 of a liquefied fuel, particularly LPG, is blown-in with hydrogen ($H_2$), particularly from a hydrogen cell 38, in the gaseous phase into an intake duct of the engine 19. The blow-in of the liquefied fuel in the gaseous phase is conducted via at least one gas blow-in-valve 17 and/or the release of gaseous hydrogen via at least one $H_2$ blow-in-nozzle 40. The intake duct (not shown) leads into the combustion chamber of the engine 19. If only gas mixture 2, 21 and the hydrogen are burnt, the fuel operation mode is bivalent. If diesel fuel or gasoline fuel is additionally and simultaneously burned, the fuel operation mode is trivalent. If only gas mixtures 2, 21 and either diesel fuel or gasoline fuel are burned at the same time, the fuel mode is bivalent. All the aforementioned fuel operation modes are possible particularly in combination with the designs described below, so that not all of these combinations are explicitly highlighted separately below.

The system comprises a gas-mixture-analysis-module 7 for determining the calorific value $H_S$ and/or the gas-mixture-characteristic value of gas mixture 2, 21, a lambda-offset-module 28 for conducting lambda-offset adjustment to bivalent or trivalent fuel mode operation, an $H_2$ module 30 for controlling or regulating hydrogen blow-in and/or a safety-module 29 for protecting the engine 19 from excessively high combustion temperatures.

In this example, no pump device is needed for conveying the gas mixture 2, 21 or $H_2$, because gas tank 3 for storing the gas mixture in the gaseous phase 21 and liquid phase 21 preferably has a pressure of at least 3 bar and/or at most 18 bar depending on the temperature and mixture composition and/or the $H_2$ hydrogen cell 38 for producing the $H_2$ gas releases the $H_2$ gas particularly at a pressure of 1 bar.

The gas-mixture-analysis-module 7 is arranged in such that it can determine the calorific value $H_S$ and/or the gas-mixture-characteristic value of the liquefied gas mixture 2, which usually results from several liquefied gases such as propane and butane.

Particularly, the gas mixture 2 is LPG according to DIN EN 589 and/or DIN EN 51622, i.e. propane comprising propene, propadiene and butane comprising iso-butane, n-butane, 1-butene, iso-butene, cis-2-butene, trans-2-butene, 1,2-butatiene, 1,3-butadiene, and/or methane-, ethane-, ethene-, neo-+iso-pentane-, n-petane-, pentene-, olefins- and C5-olefins. Such autogas or LPG is used particularly for combustion in gasoline and diesel motor vehicles engines.

Particularly, a load-dependent amount of hydrogen is preferably blown-in into the air intake duct of the engine 19 parallel to the blow-in of the gas mixture 2, 21, whereby the stratified charge produced in the combustion chamber influences the combustion process, i.e. the exhaust gases produced after combustion are reduced or minimized by the modified combustion process, particularly the exhaust pollutants and/or particle emissions from gasoline and diesel.

Load-dependent means dependent on the current engine load. The engine load is basically the ratio of the amount of work W delivered per working cycle to the displaced volume $V_H$ of a cylinder and is also called mean pressure $P_m$, which is measured in bar and is based on the following formula:
$P_m = W/V_H$ In the case of a gasoline engine, particularly an intake-manifold-pressure-sensor 43 serves to generate a load signal which reflects a value corresponding to the engine load.

In a diesel engine, a rail-pressure-sensor 44 and/or the intake-manifold-pressure-sensor 43 are used to generate the load signal which reflects the value corresponding to the engine load.

In liquefied gas mode, hydrogen is blown-in continuously into the intake duct of the engine 19, preferably in dependency of the load. Gas mixture 2, 21 is blown-in selectively and/or sequentially into the intake duct, especially in a second row in the intake duct of the engine 19, i.e. between the H2 blow-in-nozzle and the engine 19. Selectively means selectively per cylinder 19*a*, if the combustion conditions of the cylinders are different. Sequentially means that the gas mixture is blown-in at periodic time intervals. Basically, during sequential blow-in or injection, the fuel is blown-in or injected individually for each cylinder 19*a*. Usually, the blow-in or injection for all cylinders is conducted at an identical time in the course of a cylinder working cycle.

When the engine inlet valves are opened, the stored hydrogen-air mixture is first sucked into the combustion chamber, followed by the gas-mixture-air-mixture. Depending on the shape of intake duct and/or combustion chamber, the gases are mixed in the combustion chamber during combustion chamber compression. In a diesel-direct-injection-engine, the injection quantity of diesel fuel is set by the add-on control unit 18 and directly injected into the combustion chamber. In gasoline-direct-injection-engines, gasoline can be injected to cool gasoline injection valves. The add-on control unit 18 ensures that the proportions of liquefied gas fuel, liquid fuel and/or hydrogen are matched to each other for optimum combustion.

Typical applications are trucks or commercial vehicles. The system is also suitable for other applications such as combustion in engines or aggregates of boats, two-wheel, three-wheel, quad, snowmobile, snow groomers, construction machinery, tractor, agricultural and forestry machinery, emergency power generators or use in combined-heat-and-power-units.

In a gas tank 3 the gas mixture 2, especially LPG, is stored in liquid form. Above the liquid level is the vapor phase 21 of the gas mixture 2. In this case, the gas tank 3 is the gas tank of a motor vehicle which burns the gas mixture 2 in its engine 19. However, it could also be the gas tank 3 of a boat, two-wheel quad, snowmobile snow groomers, construction machinery, tractor agricultural and forestry machinery, emergency power generator or combined-heat-and-power-unit.

A multivalve 4 is arranged on the gas tank 3. The multivalve 4 provides various functions in a known way, particularly an overfill protection, a liquefied gas line 6 for the extraction of the gas mixture 2, a pressure relief valve, a remotely-controlled supply valve 51, which reduces the gas flow in case of a defect of the liquefied gas line 6, and/or a level indicator. The multivalve 4 has a float 5 for the level indicator and/or overfill protection.

Furthermore, a liquefied gas line 6 is led through the multivalve 4 into the interior of the gas tank 3 and serves to extract the gas mixture in the liquid phase 2. Upstream of the multivalve 4, the liquefied gas line 6 is electrically connected to a gas-mixture-analysis-module 7 via a conventional pressure sensor 9 and a gas-conductivity-sensor 8. In the shown embodiment of the gas-mixture-analysis-module 7, the gas-conductivity-sensor 8, the temperature sensor 1 and/or the pressure sensor 9 are arranged outside the housing of the gas-mixture-analysis-module 7 and/or measure a gas mixture 2, 21 in the liquefied gas line 6. However, the gas-conductivity-sensor 8, temperature sensor 1 and pressure sensor 9 could also be arranged in the housing of the gas-mixture-analysis-module 7 or integrated therein.

Particularly, the gas-conductivity-sensor 8 and the temperature sensor 1 are designed as one combination sensor. This saves installation space and an additional data line.

The liquefied gas line 6 is leading to a first remotely-controlled shut-off valve 10, from the gas-mixture-analysis-module 7 or depending on the arrangement of the gas-conductivity-sensor 8, temperature sensor 1 and pressure sensor 9 in the housing or outside the housing. Particularly, the first remotely-controlled shut-off valve 10 is directly connected to the evaporator/pressure-regulator 11. In the evaporator or pressure-regulator 11, the liquid gas mixture is converted into the gas phase in the evaporator chamber 55 under heat supply. The pressure-regulator-output 13 of the evaporator or pressure-regulator 11 on the low-pressure side 12 is followed by flexible line 14 through which the now gaseous gas mixture is led to the centrifugal filter 15 for cleaning the gas mixture, preferably removing ester-paraffin-olefins and/or solids. Via the outlet of the centrifugal filter 15, the gaseous gas is further fed through the connected low pressure flex line 14 particularly to the fist-distributor 16, which prevents and/or suppresses gas pressure fluctuations when withdrawing the gas mixture. The gas mixture is led in the flexible line 14 to the gas blow-in-valves 17.

The gas blow-in-valves 17 are controlled by the add-on control unit 18, particularly sequentially for gas blow-in via the control line 23, preferably with a stepped pulse, also known as peak and hold signal. Particularly, a gas temperature sensor 25 is installed in an output connection of the fist-distributor 16, wherein the gas temperature is transmitted permanently to the add-on control unit 18, preferably via electrical line 22, in order for the gas temperature to be taken into account when the gas blow-in amount is determined by the add-on control unit 18.

Particularly, an electrical line 26 is provided between add-on control unit 18 and engine control unit 20.

Generally, the engine control unit 20 is only designed for monovalent fuel mode operation, i.e. the operation of a diesel engine with diesel fuel or a gasoline engine with gasoline fuel.

Particularly, the engine control unit 20 sends the injection signal for the injection device 27, namely gasoline injection valves or diesel injectors, to the add-on control unit 18 via the electrical lines 26 or alternatively via a wireless transmission medium.

Basically, the injection signal of the engine control unit 20 is not required for the calculation of blow-in times and/or injection times by the add-on control unit 18, because the add-on control unit 18 can operate completely autarkic, self-sufficient and/or independently of the engine control unit 20.

Particularly, the add-on control unit 18 converts the injection control load signal and/or the injection time signal in the line, calculated by the engine control unit 20, into heat preferably via resistors and/or coils. Thereby, the engine control unit 20 does not recognize that the signal with the injection time has not reached an injection valve or that the line to the injection valve has been interrupted. An error message and/or malfunctions of the engine control unit 20 can thus be avoided. Preferably, the above measure is realized for gasoline engines where particularly the signal concerning the injection time calculated by the engine control unit 20 is not even recorded or processed by the add-on control unit 18, i.e. has no influence at all on the control and/or regulation by the add-on control unit 18.

In one embodiment, the signal concerning the injection time, calculated by the engine control unit 20 for a diesel engine and gasoline-direct-injection-engine, is at least recorded and optionally taken into account for controlling or regulating the blow-in time and/or injection time. The use as reference values for detecting excessively deviating calculation results in the injection time is advantageous, which can indicate, for example, a defect in the add-on control unit or a connected module or sensor.

By the detection of a terminal pin assignment of the add-on control unit 18, the add-on control unit 18 decides whether a monovalent, bivalent or trivalent fuel supply is supported, thus possible or not. This may depend, among others, on the nature of the gasoline or diesel injection system.

Particularly, the gasoline and/or diesel load characteristic stored in the add-on control unit 18 enables the add-on control unit 18 to control the injection device 27, i.e. gasoline injection valve or diesel injector.

Particularly, an intake-manifold-pressure-sensor 43 generates a load signal which preferably reflects a value corresponding to the engine load.

Particularly, a rail-pressure-sensor 44 generates the load signal in form of a pressure signal which also reflects a measure of the engine load.

The load signal measured and/or generated by the intake-manifold-pressure-sensor 43 and/or the rail-pressure-sensor 44 is fed to the add-on control unit 18.

As FIG. 2 shows for a gasoline engine and FIG. 3 for a diesel engine, the injection time of gasoline or diesel as well as blow-in times for $H_2$ and liquefied gas fuel such as LPG can be determined using the load signal from the load-dependent gas-blow-in-look-up-table.

The load-dependent gas-blow-in-look-up-table therefore corresponds to a table with values or output values stored in a storage medium, in particular injection times for gasoline or diesel as well as blow-in times for $H_2$ and liquefied gas fuel such as LPG, which can be assigned to an input value, in particular the load signal.

Further optionally, the load signal is compared with stored reference load signal values and preferably adapted to them. The load signal changed in this way can then be send back to the intake-manifold-pressure-sensor 43 or the rail-pressure-sensor 44 for the purpose of sensor calibration, for example.

The injection device 27, namely gasoline injection valve for a gasoline engine, i.e. "Otto engine", or diesel injector 27 for a diesel engine, are part of the engine 19.

Particularly, the engine 19—apart from the features resulting from this invention—is a conventional gasoline engine or diesel engine which has been retrofitted for the combustion of liquefied gas fuel and hydrogen.

Accordingly, it is understood that both the gas blow-in-valves 23 and the injection device 27, i.e. gasoline injection valves or diesel injectors, are used to introduce the respective fuel into a common combustion chamber of the engine 19 and the illustration in FIG. 1 is in this respect only schematic.

In the following, the different operating modes of the engine 19 and the way of function of the individual modules, i.e. lambda-offset-module 28, safety-module 29, $H_2$-module 30 and/or gas-mixture-analysis-module 7 are described in more detail:

Monovalent Liquid Fuel Operation, i.e. Gasoline Operation or Diesel Operation

When the engine 19 burns gasoline in the liquid fuel mode, namely in the gasoline mode, or burns diesel in the liquid fuel mode, namely in the diesel mode, this is usually introduced into the combustion chamber of the engine 19 by means of the injection device 27, i.e. gasoline injection valves or diesel injectors. The injection devices are also controlled in the usual way by the engine control unit 20. In particular, the gasoline or diesel is supplied via the gasoline or diesel tank which is not shown.

The gasoline or diesel mode can be active especially when starting the engine 19, but does not have to be, i.e. engine 19 can also be started in liquefied gas mode, thus pure liquefied gas operation, using the present invention.

The gas tank 3 has a gas-extraction-connection with valve 31, whereby gas can be led from the vaporous, i.e. gaseous, phase 21 of the gas mixture via the gas line 32 to the second remotely-controlled shut-off valve 33.

If the add-on control unit 18 has been programmed for gas start, the first remotely-controlled supply valve 51 is not actuated via control line 50, but instead the first remotely-controlled shut-off valve 10 is actuated via control line 36 and/or the second remotely-controlled shut-off valve 33 is actuated via control line 35 by the add-on control unit 18. Particularly, the add-on control unit controls the $H_2$-module 30 when gas start has been programmed.

The evaporator and/or pressure-regulator 11 now receives the gas from the vaporous phase 21 via the second remotely-controlled shut-off valve 33 and/or via the first remotely-controlled shut-off valve 10 and only operates as pressure-regulator 11.

If the evaporator or pressure-regulator 11 reaches the switch-temperature stored in the add-on control unit 18 through the motorized hot-water-supply 34, the control line 35 is de-energized, the remotely-controlled shut-off valve 33 closes and/or the remotely-controlled supply valve 51 is controlled and opened by the add-on control unit 18 via the control line 50.

In particular, the hot-water-supply 34 is connected to a cooling water line for conducting the cooling water of the engine.

If the add-on control unit 18 was not programmed for the gas start, but for a defined switch-temperature e.g. 35° C. for switching from liquid fuel mode to liquefied gas mode, then the engine is conventionally started on gasoline or diesel and operated with it until the set water temperature at the evaporator and/or pressure-regulator 11 is reached; particularly until a water temperature sensor 37 of the cooling water of the engine 19 has transmitted a water temperature above the switch-temperature to the add-on control unit 18, preferably via a signal line 38, so that the add-on control unit 18 switches from liquid fuel mode to bivalent or trivalent liquefied gas mode.

Cooling water means coolant of the engine 19 for general cooling of the engine 19.

Generally in exhaust technology, the parameter symbol Lambda stands for the air-to-fuel ratio in comparison to a combustion stoichiometric mixture. With the stoichiometric fuel ratio, there is exactly the amount of air that is theoretically required to completely burn the fuel. This is referred to as $\lambda=1$. For gasoline, the mass ratio is 14.7:1 and for a liquefied gas fuel, for example, 15.5:1.

The engine control unit 20 is connected to the lambda sensor 46 and/or a NOx sensor 45 to obtain signal values which are a measure of the completeness of the combustion. Depending on this signal value or signal values, the gasoline or diesel injection times, i.e. the time period for opening an injection valve for gasoline or diesel, are usually determined in the engine control unit 20 by means of one or more gasoline or diesel look-up-tables, which are usually stored on a storage medium of the engine control unit 20.

If more fuel is available, it is a so-called rich mixture (lambda<1), and excess air is a lean mixture (lambda>1). A lambda window (for gasoline: lambda=0.97-1.03) is the ideal area in which a catalytic converter achieves maximum cleaning performance. The lambda control usually detects the actual lambda value via a lambda sensor and changes the fuel or air volume so that the target value is set. This is necessary because fuel metering without re-measurement is not accurate enough.

As explained above on the basis of the different mass ratios, the determined and transmitted signal values differ in a comparably complete combustion process in liquid fuel mode and in bivalent or trivalent fuel mode or liquefied gas mode, e.g. with LPG and/or hydrogen. Thus, after switch to bivalent or trivalent fuel mode, the signal value of the lambda sensor 46 and/or the NOx sensor 45 no longer corresponds to the actual (real) conditions with regard to the completeness of the combustion without a signal value correction.

Thus, after switching from liquid fuel mode to a bivalent or trivalent fuel mode, the signal value without a corresponding signal value correction would no longer be suitable for the engine control unit 20 to correctly calculate the lambda ratio in the gasoline or diesel look-up-table or, in other words, to carry out a proper lambda control for efficient combustion.

In order to nevertheless enable proper lambda control by the engine control unit 20 even after switching from liquid fuel mode to bivalent or trivalent fuel mode, and thus to avoid incorrect error messages from the engine control unit 20, it is particularly provided a lambda-offset-module 28 for conducting such signal value correction, also called lambda-offset adjustment. The function and operation of the lambda-offset-module 28 is described further below.

Bivalent or Trivalent Fuel Mode or Liquefied Gas Mode

Other than in the pure monovalent liquid fuel mode namely gasoline mode or diesel mode, the bivalent or trivalent fuel mode provides the gas mixture 2, 21 and hydrogen being fed from the $H_2$ cell 38 to the air intake duct of the engine 19 for combustion. The feeding is conducted after completion of the gas start of the engine 19 via the liquefied gas line 6 and/or multivalve 4. The gas-conductivity-sensor 8, the temperature sensor 1 and/or the pressure sensor 9 of the gas-mixture-analysis-module 7 and/or the evaporator and/or pressure-regulator 11 come into direct contact with the gas mixture in the liquid phase 2. Particularly, the gas mixture in the liquid phase 2 reaches the engine 19 via the low-pressure flexible line 14, the centrifugal filter 15, the fist-distributor 16 and/or the gas blow-in-valves 17.

Particularly, hydrogen is supplied via the $H_2$ blow-in-nozzle 40.

Particularly, the liquid gas mixture 2 flows into the evaporator or pressure-regulator 11 and is converted into the gaseous state there.

Especially in the case of a cold start of the engine 19, the gas mixture can be supplied to the evaporator and/or pressure-regulator 11 in the liquid phase 2 exclusively or additionally via the gas line 6 and/or in the gaseous phase 21 via the gas line 32.

Particularly, the evaporator and/or pressure-regulator 11 only functions as a pressure-regulator when gaseous gas mixture 21 is supplied and/or the gas is transferred in the low-pressure flexible line 14 to the gas blow-in-valves 17 as described above.

The gas blow-in of the gas mixture 2 is always carried out via the gas blow-in-valves 17 and/or the $H_2$ blow-in is conducted via the $H_2$ blow-in-nozzle 40 into the air intake duct of the engine.

Particularly, the feeding into the combustion chamber in the gaseous phase is conducted particularly exclusively via the air intake duct (not shown in FIG. 1).

In current practice, in bivalent or trivalent gas combustion operation as well as in gasoline or diesel operation, the supply of the respective fuel would then only be adjusted depending on the signal of the lambda sensor or NOx sensor. This is where the lambda-offset-module 28, gas-mixtureanalysis-module 7, H$_2$-module 30 and/or safety-module 29 comes into play, whose function is described below.

Gas-Mixture-Analysis-Module 7

The gas-mixture-analysis-module 7 is used to determine the calorific value H$_S$ and/or the gas-mixture-characteristic value of the gas mixture 2, 21 particularly considering the changing composition or ratios of the individual gas components during operation. Because the changing gas mixture composition basically influences the combustion process.

The gas-mixture-analysis-module 7 therefore provides the calorific value H$_S$ and/or the gas-mixture-characteristic value of the gas mixture 2, 21 in the current composition so that the add-on control unit 18 can provide an optimized gas blow-in time for the liquefied gas fuel, the H$_2$ and/or an optimized injection time for liquid fuel.

Particularly, the gas-mixture-analysis-module 7 is connected to the gas-conductivity-sensor 8, the temperature sensor 1 and/or the pressure sensor 9.

Particularly, the gas-conductivity-sensor 8, the temperature sensor 1 and/or the pressure sensor 9 are arranged on the liquefied gas line 6. Preferably, the gas mixture 2, 21 is during operation always present either only in the liquid phase 2 particularly in liquefied gas mode, except gas start or in the gaseous phase 21 particularly during a gas start until switching to normal liquid gas operation.

Therefore, the gas-conductivity-sensor 8, the temperature sensor 1 and/or the pressure sensor 9 always only measure either the gas mixture in the liquid phase 2 or in the gaseous phase 21, i.e. basically liquid phase 2 and gaseous phase 21 not simultaneously.

Particularly, by processing the measurement data of the gas-conductivity-sensor 8, the temperature sensor 1 and/or the pressure sensor 9, the gas portions of the gas mixture 2, 21 can be determined. In particular, these gas components include propene, propadiene, iso-butane, n-butane, 1-butene, iso-butene, cis-2-butene, trans-2-butene, 1,2-butatiene, 1,3-butadiene, methane, ethane, ethene, neo-+iso-pentane, n-petane, pentene, olefins, and/or C5-olefins.

The gas-conductivity-sensor 8 is especially configured to conduct an ionization measurement.

In one embodiment, the gas-conductivity-sensor 8 is designed such that the gas-conductivity-sensor 8 measures the gas conductivity, or the electrical conductivity of the gas mixture 2, 21 respectively, particularly at a constant voltage between the anode and cathode, preferably with the aid of a measuring current. The current being measured is then a measure of the electrical conductivity and/or represents the measurement signal.

Because the current being measured is influenced by the temperature, the temperature influence can be determined and/or taken out, compensated or normalized by processing the current being measured with the measured temperature of the temperature sensor 1 in order to obtain a conductivity value independent of the temperature, in particular temperature-normalized.

The actual density of the gas mixture 2, 21 can also influence the current being measured.

The density of the current gas mixture 2, 21 is preferably determined based on the measured temperature, particularly by temperature sensor 1, and the measured pressure, particularly by the pressure sensor 9.

By processing the current being measured with the density being determined, the density influence can be determined and/or taken out, compensated or normalized in order to obtain a conductivity value that is independent of the density, particularly density-normalized.

In one advantageous embodiment, a temperature normalization and density normalization of the measurement signal of the gas-conductivity-sensor 8 can be combined to determine a normalized calorific value H$_S$ and/or a normalized gas-mixture-characteristic value. Preferably, the calorific value H$_S$ and/or the gas-mixture-characteristic value determined in this way is transmitted to the add-on control unit 18 in order to be considered when determining the gas blow-in time, alternatively or optionally also the gas blow-in amount.

Alternatively, by processing the current being measured with the measured pressure of the pressure sensor 9, the pressure influence can be determined and/or taken out, compensated or normalized in order to obtain a conductivity value independent of the pressure, particularly pressure-normalized.

Particularly, a temperature normalization, density normalization and/or pressure normalization of the measurement signal of the gas-conductivity-sensor 8 can be combined in order to determine a temperature-normalized, density-normalized and/or pressure-normalized calorific value H$_S$ and/or gas-mixture-characteristic-value, which could then be transmitted to the apparatus or add-on control unit 18 for determining the gas blow-in time, alternatively or optionally the gas blow-in amount.

Preferably, in the gas-mixture-analysis-module 7, it is stored a particularly multidimensional gas-mixture-analysis-look-up-table, which allows an allocation of the calorific value H$_S$ and/or gas-mixture-characteristic value based on the measurement signal of the gas-conductivity-sensor 8, the determined density of the gas mixture 2, 21 and/or the temperature signal of the temperature sensor 1.

Preferably, the properties of the typical gas components of the liquefied gas fuel are taken into account in the particularly multi-dimensional gas-mixture-analysis-look-up-table, so that the calorific value H$_S$ being output and/or the gas-mixture-characteristic value being output have considered the gas composition of the current gas mixture 2, 21.

Preferably, the data stored in the particularly multidimensional gas-mixture-analysis-look-up-table have been determined by one or more series of measurements and/or allocate the calorific value H$_S$ and/or the gas-mixture-characteristic value in dependency of different mixing ratios of the individual gas components based on the electrical conductivity of the gas mixture 2, 21 preferably after normalization of the measured electrical conductivity with respect to a defined temperature and a defined density, alternatively or optionally also to a defined pressure.

Alternatively, the calorific value H$_S$ and/or gas-mixture-characteristic value can be assigned by an algorithm which solves a multidimensional equation system. Such a decomposing determination of the calorific value H$_S$ and/or the gas-mixture-characteristic value is similar to a Fourier analysis at frequencies. Because the density, temperature and/or conductivity reflect the property of all gas components together, i.e. the sum or the integral over the individual gas components, whereby each gas component has a different density, temperature and/or conductivity for itself.

When measuring the gas conductivity, i.e. the electrical conductivity, positive and/or negative ions particularly in a gas mixture 21 in the gaseous phase contribute to the conduction of the electrical current.

In one embodiment, the gas-conductivity-sensor 8 has an anode and a cathode to measure the conductivity of the gas mixture 2, 21. Such a gas-conductivity-sensor 8 can be provided with very little manufacturing effort.

The ionization measurement, or the gas-conductivity-sensor 8 and the temperature sensor 1, can be used to determine particularly the gas density, thermal conductivity and/or effective resistances of the gas mixture 2, 21. These measurement data of the gas-conductivity-sensor 8 and the temperature sensor 1 are transferred to the gas-mixture-analysis-module 7 particularly as an analog voltage signal of at least 0.5 and/or at most 4.5 V, especially in the embodiment with a combination sensor. Particularly, it is converted there into a digital 8 bit signal. Alternatively, the gas-conductivity-sensor 8 can also include an analog-to-digital-converter and/or provide a digital signal.

The gas-mixture-analysis-module 7 determines the calorific value $H_S$ and/or the gas-mixture-characteristic value based on the measurement signal of the gas-conductivity-sensor 8, the temperature sensor 1 and/or the pressure sensor 9.

Particularly, the calorific value $H_S$ and/or the gas-mixture-characteristic value are preferably transmitted further to the add-on control unit 18 via the signal/control line 24 or a wireless transmission means.

Particularly, a gas-mixture-regulating-look-up-table (FIG. 4) is stored in the add-on control unit 18, which allows determination of a gas-mixture-adjustment-factor as output parameter, preferably with percentage as unit, based on the calorific value $H_S$ as input parameter. Alternatively, the gas-mixture-regulating-look-up-table can output the gas-mixture-adjustment-factor based on the gas-mixture-characteristic value as input parameter.

Particularly, this gas-mixture-adjustment-factor is used with the blow-in time, as determined in above described manner, for the liquefied gas fuel, in particular. Preferably, the gas-blow-in-look-up-table is shifted by the gas-mixture-adjustment-factor, i.e. in the direction of rich or lean, to obtain an optimized blow-in time being adapted to the composition of the gas mixture 2, 21, as shown in FIG. 5.

Particularly, the pressure sensor 9 is used to measure the pressure in the liquefied gas line 6, in which the gas mixture can be present basically either in the liquid phase 2 or in the gaseous phase 21. It is the pressure prevailing in the liquefied gas line 6 and is needed for calculating and/or compensating the flow density and/or gas density of the gas mixture or the gas components in the gas mixture.

Thus, measured values from the gas-conductivity-sensor 8, the temperature sensor 1 and/or the pressure sensor 9 with information about the gas mixture 2 in the liquefied gas line 6 are transmitted to the gas-mixture-analysis-module 7. From these sensor data, the gas-mixture-analysis-module 7 determines the calorific value $H_S$ and/or the gas-mixture-characteristic value as described above as a variable voltage parameter, i.e. a voltage signal which is preferably fed analog or digital via the signal or control line 24 to the add-on control unit 18 in order to determine the gas-mixture-adjustment-factor in percentage for optimizing the gas blow-in time via the gas-mixture-regulating-look-up-table. In this way, the gas blow-in time is controlled based on the current gas mixture composition or mixing ratios of the gas mixture 2, 21.

The gas-conductivity-sensor 8 and the temperature sensor 1 measure, by ionization, the density thermal conductivity and effective resistances of the gas mixture 2 or of the vapor phase 21 consisting of the gases propene, propadiene, iso-butane, n-butane, 1-butene, iso-butene, cis-2-butene, trans-2-butene, 1,2-butatiene, 1,3-butadiene, methane, ethane, ethene, neo-+iso-pentane, n-petane, pentenes, olefins and/or C5-olefins.

Particularly, the gas-mixture-analysis-module 7 is equipped in terms of hardware and software such that it can, based on the measured values of the gas-mixture-analysis-module 7, determine a current calorific value $H_S$ and/or gas-mixture-characteristic value and/or optionally a current mixing ratio of the gases or gas components of the gas mixture in the liquid phase 2 and/or vapor phase 21, i.e. the gas mixture composition.

The determined calorific value $H_S$ and/or the gas-mixture-characteristic value of the gas mixture 2, 21 can be transmitted analogously or digitally via the electrical line 24 to the add-on control unit 18.

In particular, a gas-mixture-regulating-look-up-table is stored in the add-on control unit 18, in which a gas-mixture-adjustment-factor is assigned preferably as a percentage value, in particular for the bivalent gas blow-in amount in dependency of the calorific value $H_S$ and/or the gas-mixture-characteristic value.

The exact structure and way of regulation of the gas-mixture-regulating-look-up-table is described below.

Depending on the determined current calorific value $H_S$ and/or the gas-mixture-characteristic value of the gas mixture 2, 21 and the resulting gas-mixture-adjustment-factor, an determined optimized particularly bivalent LPG gas blow-in amount is then provided through the gas blow-in-valves 17, particularly parallel to the $H_2$ blow-in via the $H_2$ blow-in-nozzle 40, into the air intake duct of the engine 19 that sucks in the bivalent or trivalent fuel mixture so as to ensure proper combustion, which regulates combustion with a view to as complete combustion as possible while taking into account the current gas mixture composition.

Regulation in Defined Time Intervals

The gas-mixture-analysis-module 7 is preferably designed such that the determination of the current calorific value $H_S$ and/or gas-mixture-characteristic value of the gas mixture 2, 21 is repeated in defined time intervals.

Preferably, in case of programmed gas start, the gas-mixture-analysis-module 7 will permanently determine the gas composition and/or continuously send a calorific value $H_S$ and/or a gas-mixture-characteristic value to the add-on control unit 18 when the engine 19 is started, in order to be able to regulate the bivalent or trivalent gas injection as quickly as possible. Preferably such a permanent measurement and/or continuous transmission is active until the stored hot water temperature of the cooling water of the engine 19 is reached, which is measured in particular by the water temperature sensor 37. Once the specified water temperature has been reached, the measurements are merely carried out several times, in time intervals, when the engine 19 is running.

In particular, the measuring time interval is 30 seconds, i.e. every 30 seconds a current calorific value HS and/or gas-mixture-characteristic is provided based on current measurements. This repeated measurement and the corresponding control via the gas-mixture-regulating-look-up-table result in various advantages, as further described in the following.

Thanks to the fact that the calorific value $H_S$ and/or gas-mixture-characteristic of the gas mixture 2, 21 is determined and that the gas-mixture-regulating-look-up-table of the add-on control unit 18 is dependent on the calorific value $H_S$ and/or the gas-mixture-characteristic value of the gas mixture 2, 21, it is ensured that a proper gas combustion process takes place in the engine 19 independently of the gas mixture 2 at the beginning of the particularly bivalent gas combustion operation optional also after refueling the gas tank 3.

Thanks to the repeatedly conducted measurements and regulation during operation, temperature fluctuations are additionally considered such as those caused by wind, parking the vehicle in the sun, parking the vehicle in a garage and/or subsequent operation at sub-zero temperatures, etc. The temperature of the gas mixture is changed in order to ensure that the gas mixture is burned properly. These temperature differences of the liquid or gaseous phase in the liquefied gas line 6, particularly in the liquid phase 2, which lead to a change in the density of the refueled gas mixture, are transmitted with the signals of the gas-conductivity-sensor 8, temperature sensor 1 and/or the pressure sensor 9 to the gas-mixture-analysis-module 7 and preferably via the signal or control line 24 to the add-on control unit 18 and/or taken into account by means of the gas-mixture-regulating-look-up-table with the aim of complete combustion.

Another significant advantage is that the engine control unit 20, which permanently continues to operate also in bivalent or trivalent gas combustion mode, does not unintentionally adjust the gasoline or diesel look-up-table stored there, because, for example, the lambda values from liquefied gas fuel combustion are regarded to be lambda values from gasoline or diesel combustion.

$H_2$-Module 30

The $H_2$-Module 30 is preferably activated via the control or signal line 52 or via a wireless transmission medium by the add-on control unit 18 in liquid fuel mode when starting the engine. The add-on control unit 18 has a gas-amount-look-up-table map which can determine an amount of hydrogen based on the load value, which is preferably transmitted to the $H_2$-module via the control or signal line 52. Particularly based on this hydrogen amount, the $H_2$-Module 30 initiates the release of this hydrogen amount by the $H_2$ cell.

Particularly, the hydrogen amount is continuously blown-in into the intake duct of the engine 19 via the $H_2$ blow-in-nozzle 40 and/or is sucked in by the engine 19 through the suction pipe pressure for being supplied to the combustion chamber for combustion.

The hydrogen serves on the one hand as fuel and on the other hand to reduce harmful emissions. Because hydrogen can be burned almost free of pollutants or at least with particularly low pollutant generation. The greater the proportion of hydrogen in a bivalent or trivalent fuel mode, the lower the total amount of pollutants produced by the simultaneous combustion of two or three different fuels.

The gas-amount-look-up-table is stored in the add-on control unit 18, in particular on a storage medium. The hydrogen amount is always transmitted to the $H_2$-module in the form of an analogue or digital signal.

In addition to the load value, the gas-amount-look-up-table preferably has also the speed of the engine as input parameter. Particularly, these input parameters preferably trigger, through the hydrogen amount being transmitted to the $H_2$-module, a current control by the $H_2$-module, which splits an $H_2$-gel or water located in the $H_2$ cell 38 into hydrogen and oxygen by electrolysis. Preferably, the maximum efficiency achieved is approx. 75% hydrogen content. The particularly continuous supply of hydrogen gas or hydrogen blow-in via the $H_2$ blow-in-nozzle 40 is thus defined by the current control.

Preferably, the $H_2$-module 30 is connected with a knock sensor 39. A knock sensor 39 is optionally an acoustic sensor for the detection of a knocking noise, which is usually caused by an uncontrolled self-ignition of the air-fuel mixture besides the actual flame front. Preferably, the knock sensor 39 monitors the bivalent or trivalent stratified charge combustion processes permanently or continuously. If knocking burns are detected by the knocking sensor 39 and reported to the $H_2$-module 30, a knocking signal is transmitted from the $H_2$-module 30 to the add-on control unit particularly via the signal/control line 52. The knock signal is always transmitted to the $H_2$-module and/or to the add-on control unit 18 in the form of an analogue or digital signal.

Preferably a knock signal serves as input parameter of the gas-amount-look-up-table. Particularly, the gas-amount-look-up-table is configured such that the hydrogen amount or the current control for the production of hydrogen is preferably reduced stepwise and/or as a percentage until knock-free combustion is achieved.

Preferably, the gas-amount-look-up-table is designed such that after twenty knock-free burnings, the hydrogen amount or the current control for the production of hydrogen is preferably increased stepwise and/or as a percentage until it is reached again the hydrogen amount without having taking knock messages into account.

Preferably, the add-on control unit 18 is configured such that the add-on control unit 18 adaptively changes the gas-amount-look-up-table per step until the next restart of the engine, when the add-on control unit 18 detects the aforementioned knocking combustion processes during a driving cycle with readjustment. Preferably after restarting the engine, the control characteristic curve in the add-on control unit 18 or the hydrogen amount resulting from the gas-amount-look-up-table is again approached per step up to the knock limit, particularly as a percentage, to reposition particularly the control characteristic curve in the gas-amount-look-up-table.

In FIG. 1, the introduction of a storage or tank for the respective $H_2$ gel or water into the $H_2$ cell is only schematically shown.

Lambda-Offset-Module 28

The lambda-offset-module 28 preferably has electrical connections for in particular the following exhaust gas measuring probes: zirconium dioxide measuring probe, titanium dioxide measuring-probe, planar measuring probe as lambda sensor 46, Nerst measuring probe, LSU measuring probe as lambda sensor 46, pump-probe and/or NOx sensor 45.

Particularly, voltage and/or current look-up tables are stored in the lambda-offset-module 28 to detect the corresponding exhaust gas probe and record measurement values.

The zirconium dioxide exhaust probe as Lambda sensor 46 is a voltage emitting measuring probe. Preferably, lambda sensor 46, particularly the zirconium dioxide exhaust probe, and/or NOx sensor 45 can provide an operating range of at least −100 mV (rich exhaust gas) and/or at most 900 mV (lean exhaust gas), particularly at an working temperature range or operating temperature of at least 500° C. and/or at most 800° C., preferably approx. 650° C. Preferably, the zirconium dioxide exhaust probe 46 is doped with arsenic to work in the inverted range of at least −100 mV (lean exhaust gas) and/or at most 900 mV (rich exhaust gas). Preferably, a voltage of 5000 mV+/−10 mV is applied preferably to the lambda sensor line of the zirconium dioxide exhaust probe 46 by engine control unit 20, particularly in gasoline mode, so that the zirconium dioxide exhaust probe works as lambda probe 46 in a control range of at least 4500 mV (rich exhaust gas) and/or at most 5500 mV (lean exhaust gas) or inverted by at least 4500 mV (lean exhaust gas) and/or at most 5500 mV (rich exhaust gas). This voltage value change indicates a defined rich or lean exhaust gas mixture and is used by the engine control unit 20 to regulate the amount of fuel to be injected, in particular in addition to other regulation variables.

The titanium dioxide exhaust probe as lambda sensor 46 is preferably a resistance measuring probe. The engine control unit 20 applies a voltage of in particular 5000 mV+/−10 mV and/or at an working temperature range/operating temperature of at least approx. 650° C., the titanium dioxide exhaust probe 46 operates in a control range of at least 4500 mV (rich exhaust gas) and/or at most 5500 mV (lean exhaust gas) or inverted by at least 4500 mV (lean exhaust gas) and/or 5500 mV (rich exhaust gas). This voltage value change indicates a defined rich or lean exhaust gas mixture and is used by the engine control unit 20 to regulate the amount of fuel to be injected.

The Planar Exhaust Gas Probe as Lambda probe 46 is a current probe with a measuring cell and/or a pump cell. The working temperature range/operating temperature is in particular 500° C. to 800° C., preferably ca. 650° C., wherein the target value for the cell compensation voltage is preferably 400 to 500 mV, preferably 450 mV. If the voltage in the measuring cell deviates from this value, the pump cell creates compensation until the target value is reached again. Particularly, this compensation results in a current flow which can be at least −3.5 mA (rich exhaust gas) and/or at most 3.5 mA (lean exhaust gas). This change in current value indicates a defined rich or lean exhaust gas mixture and/or is used by the engine control unit 20 to regulate the amount of fuel to be injected.

The Nerst exhaust probe as Lambda probe 46 is also called broadband probe and/or is a current probe with a defined internal resistance, whereby zirconium dioxide, preferably zirconium (IV) oxide, is used particularly as the membrane for the pump cell opposite the measuring cell. Usually, the Nernst voltage is regulated constantly, preferably at a minimum of 2400 mV (rich exhaust gas) and a maximum of 3200 mV (lean exhaust gas). This basically corresponds to a pump current of at least 0 µA (rich flue gas) and/or at most 100 µA (lean flue gas). This change in current value signals a defined rich or lean exhaust gas mixture and is used by the engine control unit 20 with reference to the initial voltage to regulate the amount of fuel to be injected.

The LSU exhaust probe as NOx probe 45 is also called broadband probe, but is especially a planar $ZrO_2$ two-cell boundary current probe. The LSU exhaust probe comprises two cells and/or a potentiometric oxygen concentration cell of the Nernst type and/or an amperometric oxygen pump cell. The components of the exhaust gas can diffuse through the diffusion channel to the electrodes of the pump and Nernst cell, where they are brought into thermodynamic equilibrium. The control electronics record the Nernst voltage $U_N$ of the concentration cell and/or supply the pump cell with a variable pump voltage Up. If $U_N$ values are lower than the target value of particularly approx. 450 mV, the exhaust gas is lean and the pump cell is supplied with such a current that oxygen is pumped out of the duct. With rich exhaust gas, on the other hand, $U_N$ is larger than the target value and the current direction is reversed so that the cell pumps oxygen into the duct. This current value change is used in engine control unit 20 for Lambda field control, preferably of at least −3.5 mA (rich exhaust) and/or at most 4.5 mA (lean exhaust). The LSU exhaust probe is particularly suitable for diesel exhaust gas measurement, as the Lambda measuring range from 0.65 (rich exhaust gas) to 10 (lean exhaust gas/air) can be covered.

NOx measuring probes 45, as they are generally offered and found in motor vehicles, work essentially similar to broadband probes. In the first cell (pump cell), oxygen atoms still present are ionized and pumped away by the ceramic. In the second cell, the nitrogen oxides are decomposed in the same exhaust gas stream using a catalytically active substance and the oxygen content (partial pressure) is measured. The oxygen now present must have been produced by decomposing the nitrogen oxides. Thus the nitrogen oxides can be traced back. The change in current value is transmitted to the engine control unit 20 and evaluated to determine whether the burned fuel was too rich or too lean and/or which nitrogen oxide content is present in the exhaust gas.

In bivalent or trivalent liquefied gas mode, particularly with LPG and/or hydrogen, the NOx sensor 45 and/or lambda sensor 46 send a measurement value to the lambda-offset-module 28 depending on the control mode and/or in conjunction with proportions of gasoline or diesel fuel, wherein the measurement value is not correlating properly with the actual lambda ratio and/or nitrogen oxide ratio due to the different chemical properties of liquid fuel and liquefied gas fuel. As initially described, the obtained measurement data are thus not suitable for the engine control unit 20 in order to correctly process or calculate the lambda ratio or nitrogen oxide ratio in the gasoline or diesel look-up table and/or to carry out proper lambda control.

The preferably integrated lambda-offset-module 28, which is arranged particularly between the engine control unit 20 and the NOx sensor 45 and/or the lambda sensor 46, enables that the measurement signals of the NOx sensor 45 and/or lambda sensor 46 are transmitted directly to the lambda-offset-module 28 in bivalent or trivalent fuel mode, for example based of LPG, hydrogen and/or gasoline or diesel.

In one embodiment, the lambda-offset-module 28 is directly connected to the add-on control unit 18, particularly parallel to the connection to the engine control unit 20.

In the lambda offset module 28 is carried out a signal value correction for lambda-offset adjustment of the measurement signals, which are transmitted from the lambda sensor 46 and/or NOx sensor 45, with respect to the changed conditions in bivalent or trivalent fuel mode operation, particularly empirically, i.e. by processing with empirical reference values or curves, and/or by a Lie-algebral-homomorphism in connection with the Brettschneider formula via a lambda/NOx offset-look-up-table.

In one embodiment, a signal value correction for lambda-offset adjustment of the measurement signals, which are transmitted from the lambda sensor 46 and/or the NOx sensor 45, is performed by an offset-look-up-table, particularly of the lambda-offset module 28.

The measurement signals transmitted from the NOx sensor 45 and/or lambda sensor 46 are transmitted to the add-on control unit 18, preferably via the data line 48, for signal value correction, particularly directly to the lambda-offset-module 28. Preferably, the measured values are transmitted to the engine control unit 20 in parallel and/or simultaneously after the signal value correction for lambda-offset adjustment by the lambda-offset-module 28, preferably via signal line 49. The engine control unit 20 in turn can reliably control the injection time for liquid fuel based on the corrected measurement values of the Lambda-offset module 28 even in bivalent or trivalent fuel mode.

Particularly, a signal line from the engine control unit 20 for activating the injection valves for injecting a liquid fuel into the engine 19 is not directly connected to the injection valves, but only indirectly via the add-on control unit 18. This ensures that in liquefied gas operation the engine control unit 20 cannot control the injection valves for opening or closing if the add-on control unit 18 blocks this. A malfunction of the liquefied gas mode operation by the engine control unit 20 can thus be avoided.

Through this double-track control procedure, the engine control unit 20 always receives the correctly corrected measurement values based on the measurement signals of the lambda sensor 46 and/or NOx sensor 45 for bivalent or trivalent liquefied gas mode. The engine control unit 20 therefore does not create any misleading gasoline or diesel look-up-tables.

Safety-Module 29

The safety-module 29 serves to protect the engine 19 from excessively high combustion temperatures. Particularly, the safety-module 29 is connected to a knock sensor 41 and/or an exhaust-gas-temperature-measuring-probe 42. Through bivalent mode with a liquefied gas fuel, particularly LPG, and hydrogen, or in trivalent fuel mode with additional gasoline or diesel, a laminar or turbulent flame temperature of up to approx. 3100° C. can be achieved at full load operation of the engine 19. For a short time, the engine components can withstand such an increase in temperature or high temperature. However, if the engine components are exposed to such excessively high temperatures for a prolonged period of time, damage to the engine are caused by overheating of the engine components and/or of the operating fluids such as engine oil. In order to avoid an excessively high temperature or overheating of the engine due to combustion, the exhaust gas temperature in the exhaust gas flow is measured by the exhaust-gas-temperature-probe 42, particularly continuously, preferably in liquefied gas operation. If a threshold temperature is exceeded, which represents a limit to an excessively high temperature, the safety-module 29 detects that the threshold temperature has been reached and sends a warning signal to the add-on control unit 20.

Particularly, the threshold temperature for a gasoline engine is at least 800° C. and/or at most 1100° C., preferably approx. 1100° C., which generally corresponds to the exhaust gas temperature under full load.

Particularly, the threshold temperature for a diesel engine is at least 600° C. and/or at most 800° C., preferably approx. 800° C., which generally corresponds to the exhaust gas temperature under full load.

The upper limits of the threshold values given above should under no circumstances be exceeded during full load operation in bivalent or trivalent liquefied gas mode in order to avoid engine damage.

Particularly, the add-on control unit 18 is connected to the safety-module 29 preferably via the signal or control line 53. Preferably, the add-on control unit 18 transmits information to safety-module 19 as to whether the engine 19 is a gasoline engine or diesel engine, so that the threshold temperature corresponding to the engine type can be determined in safety module 29.

If the exhaust-gas-temperature-measuring-probe 42 transmits an excessively high exhaust gas temperature to the safety-module 29, i.e. above the threshold temperature, a switch-off pulse is sent via the add-on control unit 18 so that the particularly bivalent liquefied gas operation can preferably be switched off immediately.

Preferably, the add-on control unit 18 switches back to liquefied fuel mode automatically, particularly when a malfunction of the add-on control unit 18 has been detected or when no more liquefied gas fuel is available, preferably via a switch 54, which particular can indicate such a switching to the user by the position of switch 54.

Particularly, the user can deactivate the add-on control unit by manually actuating the switch 54. Then, only the engine control unit 20 is still working. This operation can then not be referred as master-slave operation, because no slave is active anymore. The add-on control unit is completely switched off, so the engine control unit works as master again.

Particularly, when the switch 54 is not in the deactivating position, the add-on control unit 18 always operates in master mode and the motor control unit 20 always operates in slave mode.

For this reason, the lambda-offset module and/or the conversion of the signal with the injection time from the engine control unit 20 into heat to simulate an intact connection to an injection valve ensures that the engine control unit 20 always remains functional, so that switching to liquefied fuel mode under control and/or regulation by the engine control unit 20 alone is possible at any time.

The knock sensor 41, which particularly is directly connected to the safety-module 29, reports every combustion process with a sensitivity of at least 18 mV/g and/or at most 34 mV/g, particularly in the measuring range of at least 1 kHz and/or at most 20 kHz. In a normal combustion process at idling to full load range in the bivalent or trivalent gas combustion operation of gasoline or diesel engines, combustion pressure oscillations between 1 kHz and 15 kHz may occur. Deciding factor for pre-damage or damage to the engine 19 is usually not the frequency of the knocking combustion but the knocking intensity. Preferably, the knock sensor 41 detects and transmits the frequency and/or the voltage output level in mV of the knocking frequency.

A voltage value of at least −450 and/or at most +450 mV is preferably stored in safety-module 29, so that when for example a threshold voltage of 900 mV Uss is exceeded, a switch-off pulse is sent to the add-on control unit 18. Particularly, the bivalent and/or trivalent fuel mode is then immediately switched off and/or the add-on control unit 18 switches back to liquid fuel mode and/or an error message is displayed via switch 54.

OBD (Onboard Diagnosis)

The add-on control unit 18 has full OBD capability of a conventional engine control unit 20 and/or an engine control unit 20 installed by the vehicle manufacturer. Particularly, the OBD data line 47 is used to exchange data with the slave engine control unit 20 for function-monitoring purposes. OBD generally describes the ability of a control unit to continuously check itself and/or the environment with regard to a given behavior or a target condition. Specifically, the legislative authority requires continuous testing of exhaust gas behavior both for a passenger car and a truck.

Particularly, a fully OBD-capable add-on control unit 18 (FIG. 7) is applied for a gasoline or diesel engine in bivalent or trivalent mode, preferably with LPG and $H_2$ gas blow-in dependency of the combustion quality $H_S$ of the gas mixture 2, 21 to be determined in conjunction with the gas start, particularly bivalent gas start, in order to achieve optimum combustion with the associated minimization of exhaust pollutants.

In one embodiment, the add-on control unit 18 is arranged retrofittable, wherein an existing engine control unit 20 is preferably operated as slave and the add-on control unit 18 is operated as master, so that the add-on control unit 18 can cause liquefied gas fuel and/or hydrogen to be blown-in independently of the engine control unit 20, preferably selectively to each cylinder 19a of the engine 19.

Particularly, in case of a naturally aspirated petrol engine—also known as a naturally aspirated or turbocharged engine—the gasoline injection nozzles or valves are switched off in gas mode operation by reprogramming the Add-on control unit 18, whereby only the liquefied gas fuel is fed to the engine particularly selectively to each cylinder 19a of the engine 19. The add-on control unit 18 works preferably based on a blow-in under consideration of a homogeneous combustion chamber charge. Because in modern diesel engines and Otto-direct-injection-engines for gasoline it is operated with the inhomogeneity of the fuel-air-mixture between Lambda 1.4 and Lambda 3, the add-on control unit 18 activates the H2-offset-module, upon which the H2 gas is, via the blow-in-nozzle for the hydrogen gas, supplied to the corresponding cylinders continuously and/or simultaneously via the air intake duct in dependency of the engine load and/or the exhaust gas behavior.

The add-on control unit 18 comprises particularly a blow-in device which can be assigned to each cylinder 19a of the engine 19 and/or serve to record the current operating status of the engine 19 during operation.

Particularly, the add-on control unit 18 comprises an integrated OBD controller or an integrated OBD control and/or OBD interface, whereby ISO and/or CAN data bus protocols are preferably supported, whereby particularly the connection to the engine control unit 20 and/or to a gasoline ECU (electronic control unit) can be established. Short-term as well as long-term integrator data for the recognition of an operating status of the engine can be obtained in this way.

Particularly, the gas blow-in of liquefied gas fuel and/or hydrogen is carried out by control and regulation processes, particularly based on the gas-blow-in-look-up-table and/or gas-amount-look-up-table, concerning a current gas blow-in that has been preceding by two gas blow-ins.

Particularly, this allows a fine adjustment of the currently calculated gas blow-in signal, i.e. the gas blow-in time or the gas blow-in amount (volume) such as the hydrogen amount.

Influencing, i.e. independent re-adjustment or re-regulation, by the engine control unit 20 does not occur in bivalent liquefied gas operation. This is enabled particularly by the add-on control unit 18 being OBD-capable and able work independently. The master mode operation with gasoline and diesel engines in liquefied gas mode is ensured by the integration of the lambda sensor 46 and/or NOx sensor 45, the lambda-offset-module 28, $H_2$-module 30 and/or safety-module 29.

Particularly, 80% LPG, 10% $H_2$ and 10% gasoline are preferably supplied to the engine 19 in the case of a gasoline-direct-injection-engine. Particularly, 70% LPG, 10% $H_2$ and 20% diesel are preferred for a diesel-injection-engine. The percentages refer either to the volume portion or weight portion.

FIG. 2 shows the bivalent gas injection control for a gasoline engine. The bivalent add-on control unit 18 detects the current engine load (vertical line at 1.4 V on the X-axis) via the voltage delivered by the intake-manifold-pressure-sensor 43. These engine load data are stored in the look-up table of FIG. 5 in an adaptable manner, i.e. as initial values for further calculation and/or further adjustment, correction and/or compensation to obtain the gas blow-in time for LPG and/or the hydrogen blow-in amount as well as other resulting output parameters such as acceleration enrichment, etc. The current engine load data (FIG. 5), the gas-mixture-regulating-look-up-table (FIG. 4) and the lambda-offset adjustment, i.e. the lambda offset control or regulation (FIG. 6), lead to the LPG gas blow-in time, which is illustrated in the upper characteristic diagram or curve in FIG. 2 and in the table in FIG. 2, bottom part, as LPG in MS.

From the adaptive engine load look-up table (FIG. 5) results particularly also the hydrogen blow-in amount, which corresponds to the lower characteristic diagram or curve in FIG. 2 and is shown in the table in FIG. 2, bottom part, as $H_2$ in [A], i.e. the signal in amperes to the $H_2$-module 38.

In a gasoline engine system of FIG. 2, no gasoline is supplied to the engine in the liquefied gas mode. Therefore, in the table in FIG. 2, bottom part, a zero is shown for "gasoline" and no curve for gasoline is shown in the diagram.

In case of a gasoline-direct-injection-system (not shown in FIG. 2), the gasoline injection time for cooling the gasoline injection nozzles is calculated as a percentage via the adaptive engine load look-up table (FIG. 5) and would be added as a third curve like with diesel in FIG. 3.

FIG. 3 shows the bivalent gas blow-in control for a diesel engine. The bivalent add-on control unit 18 detects the current engine load (vertical line at 1.0 V on the X-axis) via the voltage delivered by the rail-pressure-sensor 44. The engine load data of an intake-manifold-pressure-sensor 34 are stored adaptively in the look-up table of FIG. 5, i.e. as output values that allow to be changed, on which the further calculations and/or adjustments are based to obtain the gas blow-in time for LPG and/or the hydrogen blow-in amount as well as further resulting output parameters such as acceleration enrichment, etc. The current engine load calculation (FIG. 5), the gas-mixture-regulating-look-up-table (FIG. 4) and the lambda offset adjustment (FIG. 6) lead to the LPG gas blow-in time, which corresponds in FIG. 2 to the uppermost of the three curves at the beginning and end of the diagram and is specified in the table, bottom part, in FIG. 3 as LPG in ms.

The adaptive engine load look-up table (FIG. 5) results in the hydrogen blow-in amount, which is shown as the middle characteristic diagram or curve in FIG. 3 and is shown in FIG. 3 in the table, bottom part, as $H_2$ in [A], i.e. the signal in amperes to the $H_2$-module 38.

For ignition of the fuel in diesel engines, the diesel injection quantity to be released is calculated as a percentage via the adaptive engine load look-up table (FIG. 5), which corresponds to the lowest of the three characteristic diagrams or curves in FIG. 3 and is also shown in FIG. 3 in the table, bottom part, under the designation "Diesel".

The manufacturer or a repair shop can change the basic values in the table and the look-up tables of FIGS. 2 and 3 at any time. In the as-delivered condition, the bivalent add-on control unit 18 is preferably locked, so that it is not possible for third parties to make settings or adjustments relevant to exhaust emissions.

The gas-injection-regulating-look-up-table, which was determined based on the gas temperature, gas pressure, gas conductivity (thermal conductivity active resistance gas density), enables the gas-mixture-analysis-module 7 to provide a defined voltage signal (calorific value $H_S$ Volt shown) or a corresponding digital 8 bit signal as a measure of the gas quality. In FIG. 4, this signal defines the large point between 1.2 V and 1.4 V on the X-axis. The adaptively generated gas-mixture-regulating-look-up-table (curve or characteristic curve in FIG. 4 with discretely displayed points) indicates whether the gas blow-in time is to be increased or decreased as a percentage in order to achieve the factor lambda one of a stoichiometric combustion during gas blow-in (assuming a homogeneous mixture). For checking purposes, FIG. 4 shows the operating voltage ("supply voltage") of the gas-mixture-analysis-module 7 and the actual delivered voltage for the present gas mixture calorific value $H_S$ in volts.

FIG. 5 shows the adaptive engine load look-up table. The engine characteristic curve (upper left curve with discrete round points) is adaptively generated while driving by means of the intake-manifold-pressure-sensor 43 (negative pressure/kPa) in connection with the gas blow-in time. The diagram shown in FIG. 5 illustrates the adaptive engine load look-up table together with the gas blow-in characteristic curve (lower curve with square discrete measuring points), which was adaptively generated by means of the gas-mixture-regulating-look-up-table of FIG. 4, the lambda-offset control of FIG. 6 and the engine load determined by the intake-manifold-pressure-sensor 43. The current load point (at approx. 2.6 ms on the X-axis and approx. −36% on the Y-axis) determines the LPG gas blow-in time and the amount of hydrogen to be supplied for the gasoline engine (FIG. 2) and the diesel engine (FIG. 3).

FIG. 6 shows the lambda-offset control (lambda-offset-module 28), whereby the various probes are listed next to each other, each with a left bar as the original signal of the probe and a right bar as an adjusted signal, which is provided to the add-on control unit 18 in liquefied gas mode for adjusting the gas blow-in time and/or amount (e.g. LPG and $H_2$) according to FIG. 5. In monovalent mode, the original signal (left bar in each case) is transmitted to the engine control unit 20. The respective right bar with the Lambda signal modified or adjusted by the Lambda-offset control in one embodiment processed by reference value curves, by Lie-algebral-homomorphism in connection with Brettschneider formula is transmitted to the engine control unit 20 for further processing and/or checking, so that no unwanted and faulty Lambda look-up table changes are made in the engine control unit 20. When the liquefied gas mode is switched off, the engine can immediately continue to run monovalently without a malfunction of the engine control unit 20.

FIG. 7 shows that the add-on control unit 18 has its own fully independent OBD. All systems that influence the exhaust emissions can thereby be monitored during driving and/or the data of other control units of the vehicle, whose data is accessible via the software, can be additionally accessed. Any faults that occur are indicated to the driver by e.g. a control lamp and stored in the add-on control unit 18 as well as in the respective control unit, especially permanently. Error messages can then later be read out by a specialist repair shop via standardized interfaces. The codes (the so-called P0 codes) are defined in ISO standard 15031-6.

FIGS. 8 and 9 show exemplary flow diagrams for the processes described above. FIG. 10 shows an exemplary look-up table and illustrates the determination of an output parameter C based on input parameters A and B. C is dependent on A and B. The look-up table comprises a limited number of values for the output parameter C, each of which is assigned to a combination of values of the input parameters A and B. Particularly, the apparatus is configured such that a determination, e.g. the determined injection time, determined calorific value and/or determined gas-mixture-characteristic value, is conducted by at least one look-up table designed for this.

As described above, the information about the gas mixture, i.e. whether the gas mixture is either gaseous or liquid, particularly at the gas-conductivity-sensor 8, gas temperature sensor 1 and/or pressure sensor 9, can be determined in several ways. For example, the information about the gas mixture can be determined based on the operation mode or operating condition, thus gaseous at gas start or liquid at normal liquefied gas mode. Alternatively or additionally, the information about the gas mixture can be determined based on the position of shut-off valve 33 and/or supply valve 51. Particularly, the information is "gaseous" or is determined to be "gaseous" when the operation mode is gas start or when the supply valve (51) is closed and the second shut-off valve 33 and particularly the first shut-off valve 10 are open. Particularly, the information is "liquid" or is determined to be "liquid" when operating in the normal liquefied gas mode or when the second shut-off valve 33 is closed and the supply valve (51) and particularly the first shut-off valve 10 are open. Preferably, the position, i.e. open or closed, of an electrically controlled valve is available in the controlling unit that is provided for controlling the valve.

In one preferred embodiment, the water temperature sensor 37 at the evaporator and/or pressure-regulator is used to determine the information about the gas mixture or the aggregate state of the gas mixture. A particularly reliable determination can thus be achieved. The water temperature sensor 37 can also be used to detect a cold start and/or a warming-up.

In one preferred embodiment, the aggregate state or information is "liquid" or is determined as "liquid" if the water temperature sensor 37 measures or outputs a temperature of the gas mixture of more than 20° C., preferably more than 25° C., particularly preferably more than 30° C., hereinafter referred to as threshold-temperature. Preferably, it is then switched to normal liquefied gas operation. In one preferred embodiment, the aggregate state or information is "gaseous" or is determined as "gaseous" when the water temperature sensor 37 measures or outputs a temperature of the gas mixture below the threshold-temperature, particularly below 20° or preferably below 30° C. A particularly reliable determination of the information or aggregate state can thus be enabled.

In one preferred embodiment, an information determination unit is provided to determine the information about the gas mixture or aggregate state of the gas mixture. Normal liquefied gas mode means liquefied gas operation with liquid gas mixture and/or without gas start.

In one particularly preferred embodiment, the information about the gas mixture (gaseous or liquid) is used as input parameter for the measurement of the gas conductivity by the gas-conductivity-sensor. The configuration of the gas-conductivity-sensor can thus be adapted to the aggregate state of the gas mixture to be measured. Preferably, the voltage for measuring the gas conductivity is adapted to the aggregate state of the gas mixture to be measured. In one embodiment, a predefined first voltage for measuring a liquid gas mixture and a predefined second voltage for measuring a gaseous gas mixture are provided. Preferably, a gas-conductivity-sensor-control is provided to select a predefined voltage, particularly the first or second voltage, for the gas-conductivity-sensor to measure the gas mixture based on the information about the gas mixture or the aggregate state of the gas mixture.

In one particularly preferred embodiment, the second predefined voltage is greater than 60 volts, preferably greater than 80 volts, particularly preferred greater than 100 volts. Particularly, a predefined voltage for the gas-conductivity-sensor for measuring a gaseous gas mixture is greater than 60 volts, preferably greater than 80 volts, particularly preferred greater than 100 volts. In one embodiment, the first predefined voltage is smaller than the second predefined voltage.

Particularly, the apparatus for determining an blow-in time and/or an amount of liquefied gas fuel to be supplied to a cylinder of an engine comprises at least one processor and at least one storage medium having a program code, wherein the at least one storage medium, the at least one processor and program code are configured such that the apparatus is caused to carry out and/or control steps defined by the program code.

In one embodiment, both the gas conductivity and the information about the gas mixture or aggregate state serve as input parameters for the gas-mixture-analysis-look-up-table for determining the calorific value as output parameter.

REFERENCE SIGNS LIST 1 temperature sensor
2 gas mixture
3 gas tank
4 multivalve
5 float
6 liquefied gas line
7 gas-mixture-analysis-module
8 gas-conductivity-sensor
9 pressure sensor
10 first remotely controlled shut-off valve
11 evaporator and/or pressure-regulator
12 low-pressure side
13 line outputs
14 low-pressure flexible line
15 centrifugal filter
16 fist-distributor
17 gas blow-in-valve
18 add-on control unit
19 engine
20 engine control unit
21 gaseous phase
22 signal line for gas temperature
23 signal line for the gas blow-in-valve
24 signal line or control line for the gas-conductivity-sensor
25 gas temperature sensor
26 control line for the gasoline/diesel injection signals
27 injection device
28 Lambda-offset-module
29 safety-module
30 $H_2$-Module
31 gas-extraction-connection with valve for gas in the gaseous phase
32 gas line for gas in the gaseous phase
33 second remotely-controlled shut-off valve for gas in the gaseous phase
34 hot-water-supply for the evaporator/pressure-regulator
35 control line for the second remotely-controlled shut-off valve
36 control line for the first remotely-controlled shut-off valve
37 water temperature sensor at the evaporator/pressure-regulator
38 $H_2$ cell or hydrogen cell
39 knock sensor for the $H_2$-module
40 $H_2$ blow-in-nozzle
41 sensor for the safety-module
42 exhaust-gas-temperature-measuring-probe
43 intake-manifold-pressure-sensor
44 rail-pressure-sensor
45 NOx sensor
46 Lambda sensor
47 OBD data line
48 first Lambda-offset data line for the add-on control unit
49 second Lambda-offset data line for the engine control unit
50 control line for the remotely-controlled supply valve
51 remotely-controlled supply valve
52 signal or control line for the $H_2$-module
53 signal or control line for the safety-module
54 switch
55 evaporator chamber of the evaporator and/or pressure-regulator

The invention claimed is:

1. An apparatus for determining a blow-in time or an amount of liquefied gas fuel to be supplied to a cylinder of an engine for operating the engine in a bivalent or trivalent fuel mode, wherein the amount of liquefied gas fuel to be supplied to the cylinder of the engine can be described by the blow-in time when having a constant supply speed or flow speed of liquefied gas fuel to the cylinder, the apparatus comprising:
 a gas-mixture-regulating-look-up-table in a storage medium;
 a gas-conductivity-sensor for measuring a gas conductivity of the gas mixture of the liquefied gas fuel, wherein a measured gas conductivity is the ability of the gas mixture to conduct electrical current; and
 a processor configured to determine a calorific value based on the measured gas conductivity, to determine a gas-mixture-adjustment-factor using the gas-mixture-regulating-look-up-table and the determined calorific value or a determined gas-mixture-characteristic value, and to determine the blow-in time on the basis of the gas-mixture-adjustment-factor.

2. The apparatus of claim 1, wherein the processor determines the calorific value or the gas-mixture-characteristic value in dependency of a current composition of the gas mixture.

3. The apparatus of claim 1, wherein the gas-conductivity-sensor comprises an anode and a cathode, wherein the gas-conductivity-sensor is arranged such that for measuring the gas conductivity a constant voltage can be applied between the anode and cathode and a measuring current can be fed through the gas mixture in the liquid phase or in the gaseous phase.

4. The apparatus of claim 1, comprising a temperature sensor for measuring a temperature of the gas mixture of the liquefied gas fuel and a pressure sensor for measuring a pressure of the gas mixture of the liquefied gas fuel, wherein the calorific value or the gas-mixture-characteristic value is determined based on the measured temperature and the measured pressure.

5. The apparatus of claim 1, further comprising an add-on-module, comprising a gas-amount-look-up-table for determining the amount of hydrogen to be supplied in dependency of a current engine load and/or a current engine speed.

6. The apparatus of claim 1, wherein the gas-conductivity-sensor is configured to measure either the gas mixture in the liquid phase or in the gaseous phase.

7. The apparatus of claim 1, wherein a predefined voltage for the gas-conductivity-sensor for measuring a gaseous gas mixture is greater than 60 volts.

8. An apparatus comprising a gas-mixture-analysis-module configured to determine a calorific value of a gas mixture or a gas-mixture-characteristic value of the gas mixture depending on a current composition of the gas mixture based on a gas conductivity, a temperature and a pressure of the gas mixture by using a gas-mixture-analysis-look-up-table,
 wherein the gas-mixture-analysis-module is connected to a gas-conductivity-sensor for measuring the gas conductivity of the gas mixture of the liquefied gas fuel, and wherein the calorific value or the gas-mixture-characteristic value being determined is based on a measured gas conductivity.

9. The apparatus of claim 8, wherein the gas-conductivity-sensor is configured to measure either the gas mixture in the liquid phase or in the gaseous phase.

10. The apparatus of claim 8, wherein a predefined voltage for the gas-conductivity-sensor for measuring a gaseous gas mixture is greater than 60 volts.

11. A gas-start-system comprising:
a gas line for connection to a gas tank,
a blow-in valve operatively connected to the gas line for controlling blow-in of a gaseous phase of a gas mixture of a liquified gas fuel stored in the gas tank into a cylinder of an engine, and
a gas-conductivity-sensor for measuring a gas conductivity of the gas mixture of the liquified gas fuel, wherein the gas conductivity is the ability of the gas mixture to conduct electrical current, and
wherein the gas-start-system is arranged such that when the engine is started in a pure liquefied gas mode, only a gaseous phase of the gas mixture of the liquefied gas fuel is withdrawn from a gas tank for blow-in into the cylinder of the engine.

12. The gas-start-system of claim 11, wherein the gas-conductivity-sensor is configured to measure either the gas mixture in the liquid phase or in the gaseous phase.

13. The gas-start-system of claim 11, wherein a predefined voltage for the gas-conductivity-sensor for measuring a gaseous gas mixture is greater than 60 volts.

14. The gas-start-system of claim 11 comprising:
an evaporator or a pressure-regulator; and
a liquefied gas line that is configured to allow a liquid gas mixture of a liquefied gas fuel to flow through the liquefied gas line from the gas tank into the evaporator or the pressure-regulator in order to be converted into the gaseous state there,
wherein the gas-start-system is arranged such that when the engine is started in the pure liquefied gas mode, the gaseous phase of the gas mixture of the liquefied gas fuel is led through the liquefied gas line into the evaporator and/or pressure-regulator.

15. A method for determining a blow-in time of a first liquefied gas fuel in form of a gas mixture, or determining an amount of a second liquefied gas fuel to be supplied to a cylinder of an engine continuously, comprising:
(a1) determining the blow-in time based on an engine load or an engine speed using a blow-in-look-up-table which has been shifted towards rich or lean using either
(i) a gas-mixture-adjustment-factor determined on the basis of a calorific value or a gas-mixture-characteristic value, which in turn is determined based on an electrical gas conductivity, a temperature and a pressure of the gas mixture, the electrical gas conductivity being measured by a gas-conductivity-sensor, wherein the electrical gas conductivity is the ability of the gas mixture to conduct electrical current,
(ii) an offset-lambda value, based on a lambda value, the offset-lambda value depending on the first liquefied gas fuel, specific for a lambda sensor, or
(iii) an offset-NOx value, based on a NOx value, the offset-NOx value depending on the first liquefied gas fuel, specific for an NOx sensor, or
(a2) determining the amount of the second liquefied gas fuel to be supplied using a gas-amount-look-up-table based on the engine load or the engine speed, and
(b) increasing or reducing stepwise the blow-in time or the amount of the second liquefied gas fuel to be supplied based on a knock signal.

16. A gas-start-system comprising:
an evaporator and/or pressure-regulator; and
a liquefied gas line configured to allow a liquid gas mixture of a liquefied gas fuel to flow through the liquefied gas line from a gas tank into the evaporator or pressure-regulator in order to be converted into the gaseous state, and
means for withdrawing from the gas tank, when an engine is started in a pure liquefied gas mode, only a gaseous phase of the gas mixture of the liquefied gas fuel is withdrawn from the gas tank through the liquefied gas line for blow-in into a cylinder of the engine and is led through the liquefied gas line into the evaporator or pressure-regulator.

* * * * *